(12) United States Patent
Vinnik et al.

(10) Patent No.: US 9,610,264 B2
(45) Date of Patent: Apr. 4, 2017

(54) COMPOUNDS FOR THE TREATMENT AND PREVENTION OF RETROVIRAL INFECTIONS

(71) Applicant: KFLP Biotech, LLC, Denver, CO (US)

(72) Inventors: Andrey Vinnik, Moscow (RU); Peter Fedichev, Dolgoprudny (RU); Maxim Kholin, Moscow (RU); Christopher Molloy, Watford (GB); Aron Katz, Denver, CO (US); Alexander Kadushkin, Zheleznodorozhnyiy (RU)

(73) Assignee: KFLP BIOTECH, LLC, Denver, CO (US)

( * ) Notice: Subject to any disclaimer, the term of this patent is extended or adjusted under 35 U.S.C. 154(b) by 0 days.

(21) Appl. No.: 14/431,129

(22) PCT Filed: Sep. 26, 2013

(86) PCT No.: PCT/US2013/061940
§ 371 (c)(1),
(2) Date: Mar. 25, 2015

(87) PCT Pub. No.: WO2014/052605
PCT Pub. Date: Apr. 3, 2014

(65) Prior Publication Data
US 2015/0265557 A1    Sep. 24, 2015

Related U.S. Application Data

(60) Provisional application No. 61/705,719, filed on Sep. 26, 2012.

(30) Foreign Application Priority Data

Oct. 4, 2012    (EP) .................................... 12187169

(51) Int. Cl.
| | | |
|---|---|---|
| *A61K 31/167* | (2006.01) | |
| *A61K 31/40* | (2006.01) | |
| *A61K 31/404* | (2006.01) | |
| *A61K 31/4166* | (2006.01) | |
| *A61K 31/445* | (2006.01) | |
| *A61K 31/451* | (2006.01) | |
| *A61K 31/495* | (2006.01) | |
| *A61K 31/496* | (2006.01) | |

(52) U.S. Cl.
CPC ............ *A61K 31/167* (2013.01); *A61K 31/40* (2013.01); *A61K 31/404* (2013.01); *A61K 31/4166* (2013.01); *A61K 31/445* (2013.01); *A61K 31/451* (2013.01); *A61K 31/495* (2013.01); *A61K 31/496* (2013.01)

(58) Field of Classification Search
CPC .... A61K 31/167; A61K 31/40; A61K 31/495; A61K 31/4166; A61K 31/496; A61K 31/445; A61K 31/451; A61K 31/404
See application file for complete search history.

(56) References Cited

U.S. PATENT DOCUMENTS

2011/0086024 A1    4/2011    Arthos et al.

FOREIGN PATENT DOCUMENTS

WO    WO 2012/055987    5/2012

OTHER PUBLICATIONS

Wolff, Some consideration for prodrug design, Burger's Medicinal Chemistry and Drug Discovery, 5th Edition, vol. 1, pp. 975-977, 1995.*
Banker et al, Prodrug, Modern Pharmaceutics, 3rd Edition, pp. 451 and 596, 1996, Modem Pharmaceutics.*
PCT International Preliminary Report on Patentability issued in International Application No. PCT/US2013/061940, mailed Apr. 9, 2015.
PCT International Search Report and Written Opinion issued in International Application No. PCT/US2013/061940, mailed Nov. 22, 2013.
Teixeira et al., "Viral surface glycoproteins, gp120 and gp41, as potential drug targets against HIV-1: brief overview one quarter of a century past the approval of zidovudine, the first anti-retroviral drug," *European Journal of Medicinal Chemistry*, 46:979-992, 2011.
Tilton and Doms, "Entry inhibitors in the treatment of HIV-1 infection," *Antiviral Research*, 85:91-100, 2010.

* cited by examiner

*Primary Examiner* — Sudhakar Katakam
(74) *Attorney, Agent, or Firm* — DT Ward, PC; Donna T. Ward; Lingyun Jia

(57) ABSTRACT

The present invention provides compounds and pharmaceutical compositions for use in treating or preventing retroviral infections, in particular HIV infections and/or diseases associated with an HIV infection.

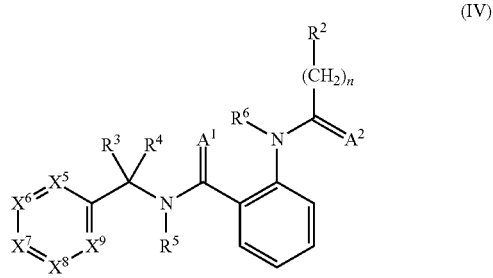

9 Claims, 2 Drawing Sheets

COMPOUNDS FOR THE TREATMENT AND PREVENTION OF RETROVIRAL INFECTIONS

Figure 1:
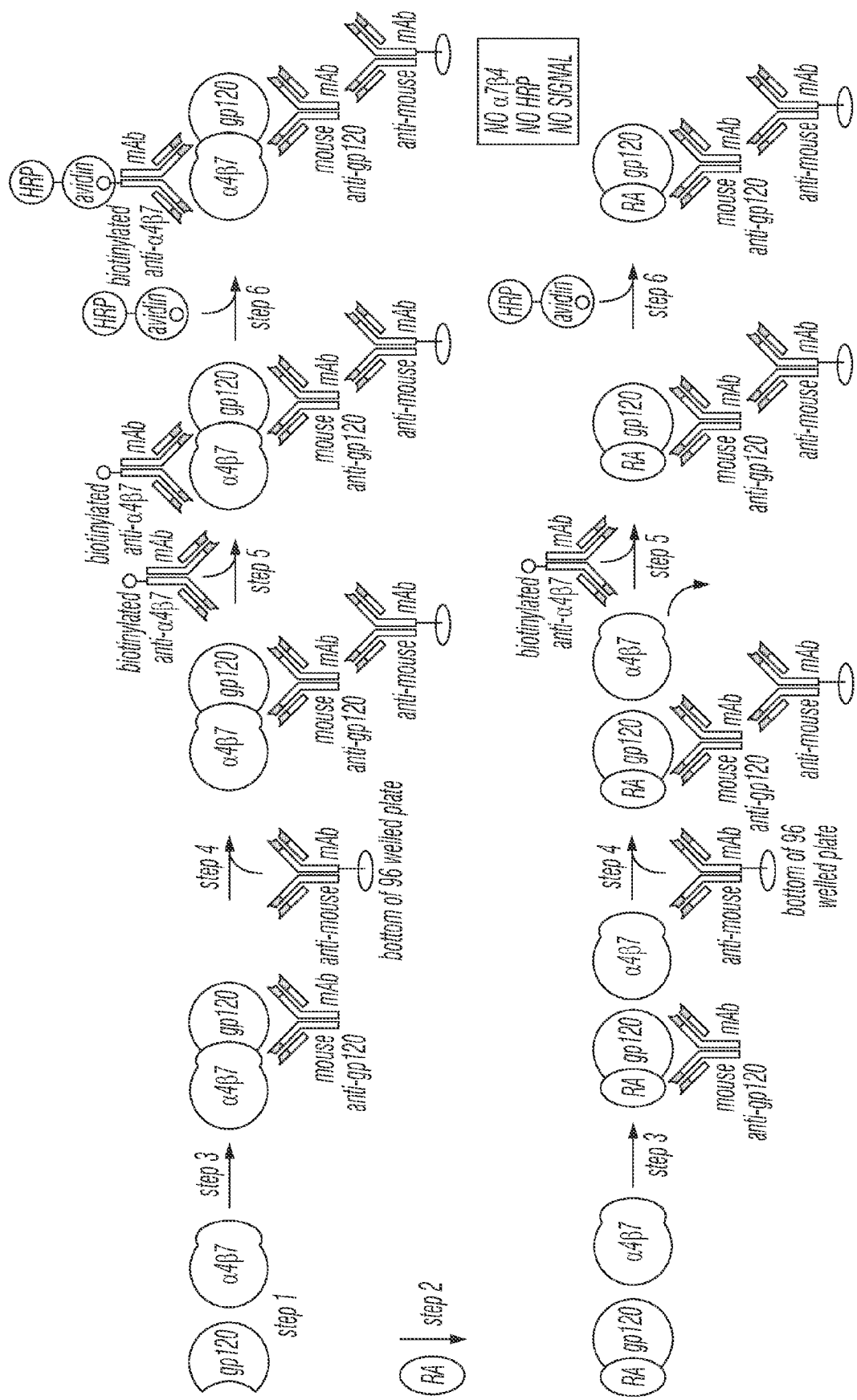

The present application is a national phase application under 35 U.S.C. §371 of International Application No. PCT/US2013/061940, filed Sep. 26, 2013, which claims benefit of priority to U.S. Provisional Patent Application No. 61/705,719, filed Sep. 26, 2012, and claims benefit of priority to European Patent Application No. 12187169.3, filed Oct. 4, 2012, the entirety of each of which are incorporated herein by reference.

The present invention provides compounds and pharmaceutical compositions for use in treating or preventing retroviral infections, in particular HIV infections and/or diseases associated with an HIV infection. Moreover, the invention relates to methods for the treatment or prevention of such infections.

Human immunodeficiency virus (HIV) is a retrovirus belonging to the primate lentiviruses that can lead upon successful infection to a condition termed acquired immunodeficiency syndrome (AIDS). Said condition is characterized in that the immune system begins to fail and therefore the patient's body becomes increasingly susceptible to secondary and/or recurring infections. The infection with HIV occurs by, e.g., transfer of blood, semen, vaginal fluid and also breast milk. Due to the presence of unbound infectious virus particles in body fluids the rate of infection is high. In particular, sexual intercourse and transmission from infected mothers to their babies as well as feeding with breast milk account for a majority of new HIV cases.

Since becoming a pandemic in the 1980's HIV has received much attention both in the general public as well as in the scientific community. The World Health Organization (WHO) and the Joint United Nations Program on HIV/AIDS (UNAIDS) have recently estimated that about 25 million people have died due to AIDS since 1981 making it one of the most destructive pandemics in history. This can be linked back to the unique way of cellular infection, manifestation and persistence of the retrovirus in the body which has not yet been found to be successfully treatable.

Presently, treatment of HIV infected patients relies on combination therapies such as, e.g., highly active antiretroviral therapy (HAART), that may be expensive, cause serious drug-related side effects and may give rise to resistant HIV strains after prolonged progression of the therapy. Conventional combination therapies comprise nucleoside-analogue reverse transcriptase inhibitors (NARTIs or NRTIs), non nucleoside-analogue reverse transcriptase inhibitors (NNRTIs) and/or protease inhibitors.

In addition to reverse transcriptase and protease inhibitors, therapeutic drugs for the treatment or prevention of HIV-related diseases have been and continue to be developed which interfere with the process of binding and entry of HIV into its target cells. The process of HI-viral entry into a target cells represents the first step in the viral infection circle. It is characterized by a complex series of events that are initiated through the binding of the viral surface glycoproteins to specific receptor molecules on the cell's outer membrane. This interaction is thought to trigger a conformational change in the viral glycoprotein, which then mediates fusion of the lipid bilayers of the cell and viral membranes and allows the genetic material of the virus to be introduced into the host-cell cytoplasm.

A more detailed view shows that CD4 is the primary receptor for HIV which is a 60 kD molecule on the surface of certain immune cells such as, e.g., T lymphocytes, cells of the monocyte/macrophage lineage, or dendritic, antigen-presenting cells (Weiss, R. A. (1993), The Retroviridae, 2nd edition (ed. J. A. Levy), pp. 1-108. Plenum Press, New York), and is endogenously involved in T-cell activation (Sweet et al. (1991), Curr. Opin. Biotechnol. 2: 622-633). The virus enters $CD4^+$ cells and after successful amplification and budding of progeny virus particles lyses the infected $CD4^+$ cells. Hence, a hallmark of acquired immunodeficiency syndrome (AIDS) is the depletion of $CD4^+$ cells. The binding of HIV to $CD4^+$ cells involves the formation of a stable complex between CD4 and gp120, the glycoprotein exposed on the envelope of HIV that mediates binding and subsequent entry into the host cell. CD4 has shown to be necessary and sufficient for efficient HIV attachment to target cells. Nevertheless, its presence alone is not sufficient for viral entry and the importance of secondary/fusion receptors could subsequently be established that mediate the fusion of the virus particle and the target cell. This requirement of the presence of a secondary/fusion receptor appears to be so far unique to primate lentiviruses. Several studies identified the CXCR4 and the CCR5 receptor which have been shown to mediate the fusion of virus particles with different tropisms and the respective target cell. The CXCR4 receptor seems to be specific for T-cell tropic HIV strains whereas the CCR5 receptor seems to be specific for M-tropic strains.

In detail, HIV enters macrophages and $CD4^+$ T cells by the adsorption of glycoproteins on the target cell followed by fusion of the viral envelope with the cell membrane and the release of the HIV capsid into the cell (Chan D et Kim P, Cell 93 (5): 681-4 (1998); Wyatt R et Sodroski J, Science 280 (5371): 1884-8 (1998). The first step in fusion involves the high-affinity attachment of the CD4 binding domains of gp120 to CD4. Once gp120 is bound to CD4, the envelope complex undergoes a profound conformational change, exposing the chemokine binding domains of gp120 and allowing them to interact with the target chemokine receptor (generally either CCR5 or CXCR4, but others are known to interact). This results in a more stable two-pronged attachment, which allows the N-terminal fusion peptide gp41 to penetrate the cell membrane.

Thus, the gp120/CD4 interaction in connection with the subsequent interaction with the above-identified coreceptors CXCR4 and CCR5 provides a potential target for intervention in HIV infections. A number of antibodies and small molecules have been developed as blockers or inhibitors of the gp120/CD4 binding by interacting with either gp120 or CD4 (Vermeire et al. (2006), Curr. Med. Chem., 13, 731). Common blockers or inhibitors include but are not limited to antisense molecules, antibodies, antagonists, traps, and their derivatives. However, so far none of these approaches has led to a clinically approved drug. Importantly none of these approaches is designed to target the conformational change undergone by gp120 after binding to CD4. In particular, compounds that are shown to interact with binding sites on the surface of gp120 next to the natural binding site for CD4 could not be shown to inhibit said conformational change (Kong et al., Biochimica et Biophysica Acta—Proteins & Proteomics. Elsevier, Netherlands, vol. 1764, no. 4, April 2006, 766-772, ISSN:1570-9639; Berchanski et al., Biochimica et Biophysica Acta—Biomembranes, Netherlands, vol. 1768, no. 9, September 2007, 2107-2119, ISSN:1570-9639).

A further receptor was demonstrated to be critically involved in the primary infection of $CD4^+$ cells (Arthos et al., Nature Immunology, vol. 9, no. 3 (2008)). It was shown that the HIV envelope protein gp120 bound to and signalled by means of integrin alpha4 beta7 on CD4+ T lymphocytes. Further, it was shown that gp120 rapidly activated LFA-1, an integrin that facilitates HIV infection, on CD4+ T cells in an alph4 beta7-dependent way. Functioning principally as a homing receptor, alpha4 beta7 mediates the migration of leukocytes to an retention of leukocytes in the lamina propria of the gut. Thus, in the tissue where HIV preferentially replicates, its envelope interacts directly with an adhesion receptor that is specifically linked to the function of CD4+ T cells in that tissue.

As evidenced by the above discussion, the efforts to identify and develop more efficient drugs and therapies to successfully address the increasing rate of new HIV infections, of progression to AIDS and the increasing death toll linked to the latter are intense and ever increasing in view of the rapidly growing knowledge of HIV and its interaction with the human host. Despite said efforts there is still no reported success of therapeutic strategies and their technical implementation to successfully prevent or to treat HIV infection.

In the light of the above, it was the aim of the investigations leading to the present invention to identify compounds useful as active agents for the prevention or the treatment of retroviral infections, in particular HIV infections and/or diseases associated with an HIV infection.

Thus, the invention provides compounds of the following formula (I), as well as salts, solvates or prodrugs thereof

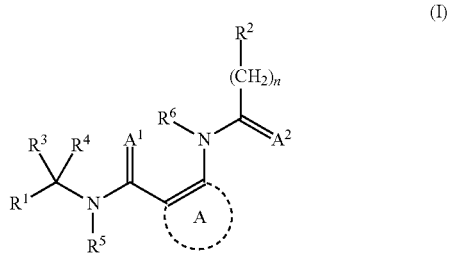

(I)

for use in preventing or treating a retroviral infection, wherein:

n is selected from 0, 1, 2 or 3;

$R^1$ represents a carbocyclic group or heterocyclic group, both of which are optionally substituted by one or more groups independently selected from C1-6 alkyl, C2-6 alkenyl, C2-6 alkynyl and C1-6 alkoxy, with any of the alkyl, alkenyl, alkynyl or alkoxy substituents being optionally further substituted with 1 to 3 fluoro atoms or with an aryl, heteroaryl, cycloalkyl or heterocycloalkyl group;

$R^2$ represents a carbocyclic group or heterocyclic group, both of which are optionally substituted, or a group $-Q^1-L^1-Q^2$, wherein $Q^1$ is a carbocyclic group or a heterocyclic group, both of which are optionally substituted, $L^1$ is absent or represents a linking group of the formula $-(CR^9R^{10})_p-$, wherein p is selected from 1, 2, 3 or 4, $R^9$ and $R^{10}$, independently for each occurrence, are selected from H and C1-6 alkyl, and wherein one or more of the $CR^9R^{10}$ moieties may be replaced by one or more groups selected from —NH—, —N(CH$_3$)—, —O—, —S—, —C(O)O—, —O—C(O)—, —C(O)—NH—, —NH—C(O)—, or —C(O)—; and $Q^2$ is a carbocyclic group or a heterocyclic group, both of which are optionally substituted;

wherein each optionally substituted carbocyclic group and each optionally substituted heterocyclic group may carry 1 to 3 substituents independently selected from C1-6 alkyl, C2-6 alkenyl, C2-6 alkynyl, oxo (═O), halogen, —CF$_3$, —CN, —NO$_2$, —NR$^{11}$R$^{12}$, —CONR$^{71}$R$^{12}$, —COR$^{11}$, —OR$^{11}$, —SR$^{11}$, —SOR$^{11}$, —SO$_2$R$^{11}$, —SO$_2$NR$^{11}$R$^{12}$, —NR$^{11}$COR$^{12}$, —NR$^{11}$SO$_2$R$^{12}$, —OCOR$^{11}$, —COOR$^{11}$, and —SO$_3$H$_2$;

and wherein each $R^{11}$ and each $R^{12}$ is independently selected from hydrogen or C1-6 alkyl;

$R^3$ and $R^4$ are independently selected from H, C1-6 alkyl, C2-6 alkenyl, C2-6 alkynyl and C1-6 alkoxy, which alkyl, alkenyl, alkynyl or alkoxy are optionally substituted with 1 to 3 fluoro atoms;

$R^5$ and $R^6$ are independently selected from H, C1-6 alkyl, C2-6 alkenyl, C2-6 alkynyl and C1-6 alkoxy, which alkyl, alkenyl, alkynyl or alkoxy are optionally substituted with 1 to 3 fluoro atoms, or one of $R^5$ and $R^6$ is as defined above, and the other one is additionally linked to A to form a heterocyclic group fused with A;

$A^1$ and $A^2$ are independently selected from O, S, NH and NOH; and the cyclic moiety A indicated by the dashed cycle in formula (I) is a carbocyclic group containing the double bond indicated in the formula which may be part of an aromatic system, or a heterocyclic group containing the double bond indicated in the formula which may be part of an aromatic system, both of which are optionally substituted by one or more groups independently selected from C1-6 alkyl, C2-6 alkenyl, C2-6 alkynyl and C1-6 alkoxy.

As used herein, "alkyl" represents a straight or branched chain saturated hydrocarbon residue which does not comprise any carbon-to-carbon double bonds or carbon-to-carbon triple bonds. As exemplary groups, methyl, ethyl, propyl and butyl are mentioned.

As used herein, "alkenyl" represents a straight or branched chain unsaturated hydrocarbon residue comprising one or more than one (such as two or three) carbon-to-carbon double bond(s) which does not comprise any carbon-to-carbon triple bonds.

As used herein, "alkynyl" represents a straight or branched chain unsaturated hydrocarbon residue comprising one or more than one (such as two or three) carbon-to-carbon triple bond(s). It will be understood that an "alkynyl" may also comprise one or more than one (such as two or three) carbon-to-carbon double bonds.

As used herein, "alkylene" represents a straight or branched chain alkanediyl group which does not comprise any carbon-to-carbon double bonds or carbon-to-carbon triple bonds.

As used herein, "alkenylene" represents a straight or branched chain alkenediyl group comprising at least one carbon-to-carbon double bond which does not comprise any carbon-to-carbon triple bonds.

As used herein, "alkynylene" represents a straight or branched chain alkynediyl group comprising at least one carbon-to-carbon triple bond and optionally comprising one or more carbon-to-carbon double bonds.

As used herein, "aryl" represents an aromatic hydrocarbon ring, in particular a 6 to 10 membered ring (unless a different number of ring members is indicated in a specific context), including bridged ring or fused ring systems containing at least one aromatic ring. Preferred as aryl groups are monocyclic groups with 6 ring members or fused bicyclic groups with 9 or 10 ring members. Thus, generally preferred embodiments of "aryl" are phenyl or naphthyl.

As used herein, "aralkyl" represents an alkylene group as defined above, carrying an aryl group at one of its valencies.

As used herein, "heteroaryl" represents an aromatic ring, preferably a 5-14 membered ring (unless a different number of ring members is indicated in a specific context), including bridged ring or fused ring systems containing at least one aromatic ring, comprising one or more (such as, e.g., one, two, or three) ring heteroatoms independently selected from O, S, and N. Particularly preferred as heteroaryl groups are monocyclic groups with 5 or 6 members and fused bicyclic groups with 8 to 10 ring members. "Heteroaryl" may, for example, refer to thienyl (thiophenyl), benzo[b]thienyl, naphtho[2,3-b]thienyl, thianthrenyl, furyl (furanyl), isobenzofuranyl, chromenyl, xanthenyl, phenoxathiinyl, pyrrolyl (including, without limitation, 2H-pyrrolyl), imidazolyl, pyrazolyl, pyridyl (pyridinyl; including, without limitation, 2-pyridyl, 3-pyridyl, and 4-pyridyl), pyrazinyl, pyrimidinyl, pyridazinyl, indolizinyl, isoindolyl, indolyl (including, without limitation, 3H-indolyl), indazolyl, purinyl, isoquinolyl, quinolyl, phthalazinyl, naphthyridinyl, quinoxalinyl, cinnolinyl, pteridinyl, carbazolyl, beta-carbolinyl, phenanthridinyl, acridinyl, phenanthrolinyl (including, without limitation, [1,10]phenanthrolinyl, [1,7]phenanthro-linyl, and [4,7]phenanthrolinyl), phenazinyl, isothiazolyl, phenothiazinyl, oxazolyl, isoxazolyl, furazanyl, phenoxazinyl, pyrazolo[1,5-a]pyrimidinyl (including, without limitation, pyrazolo[1,5-a]pyrimidin-3-yl), 1,2-benzoisoxazol-3-yl, or benzimidazolyl.

As used herein, "cycloalkyl" represents a saturated hydrocarbon ring, preferably a 3-11 membered ring (unless a different number of ring members is indicated in a specific context), including bridged ring, spiro ring or fused ring systems. "Cycloalkyl" may, for example, refer to cyclopropyl, cyclobutyl, cyclopentyl, cyclohexyl, or cycloheptyl. Preferred as cycloalkyl groups are monocyclic groups with 5 or 6 ring members or fused bicyclic groups with 9 or 10 ring members.

As used herein, "heterocycloalkyl" represents a saturated ring, preferably a 3-11 membered ring (unless a different number of ring members is indicated in a specific context), including bridged ring, spiro ring or fused ring systems, containing one or more (such as, e.g., one, two, or three) ring heteroatoms independently selected from O, S, and N. Particularly preferred as heterocycloalkyl groups are monocyclic groups with 5 or 6 members and fused bicyclic groups with 8 to 10 ring members. "Heterocycloalkyl" may, for example, refer to oxetanyl, tetrahydrofuranyl, piperidinyl, piperazinyl, aziridinyl, azetidinyl, pyrrolidinyl, imidazolidinyl, morpholinyl, pyrazolidinyl, tetrahydrothienyl, octahydroquinolinyl, octahydroisoquinolinyl, oxazolidinyl, isoxazolidinyl, azepanyl, diazepanyl, oxazepanyl or 2-oxa-5-aza-bicyclo[2.2.1]hept-5-yl.

As used herein, "arylene" represents an aryl group, as defined herein above, which is divalent (i.e., has two points of attachment to the remainder of the molecule). "Arylene" may, for example, refer to phenylene (i.e., a —$C_6H_4$— group; including, e.g., phen-1,2-diyl, phen-1,3-diyl, and phen-1,4-diyl).

As used herein, "heteroarylene" represents a heteroaryl group, as defined herein above, which is divalent (i.e., has two points of attachment to the remainder of the molecule).

As used herein, "cycloalkylene" represents a cycloalkyl group, as defined herein above, which is divalent (i.e., has two points of attachment to the remainder of the molecule).

As used herein, "heterocycloalkylene" represents a heterocycloalkyl group, as defined herein above, which is divalent (i.e., has two points of attachment to the remainder of the molecule).

As used herein, a "carbocyclic group" or "carbocycle" represents a ring formed by carbon atoms as ring members, preferably a 3-14 membered ring, including bridged ring, spiro ring or fused ring systems. The ring members may be linked by single bonds or double bonds, including aromatic bonds. Preferred are monocyclic groups with 5 or 6 or fused bicyclic rings with 8 to 10 ring members. The "carbocyclic group" or "carbocycle" encompasses as preferred embodiments the aryl, the cycloalkyl, the arylene and the cycloalkylene group as defined above, depending on the required valency of the carbocyclic group which will be readily apparent to the skilled person.

As used herein, a "heterocyclic group" or "heterocycle" represents a ring containing carbon atoms and one or more (such as, e.g., one, two, or three) heteroatoms independently selected from O, S, and N as ring members, preferably a 3-14 membered ring, including bridged ring, spiro ring or fused ring systems. The ring members may be linked by single bonds or double bonds, including aromatic bonds.

Preferred are monocyclic groups with 5 or 6 or fused bicyclic rings with 8 to 10 ring members. The definition of the term "heterocyclic group" or "heterocycle" encompasses as preferred embodiments the heteroaryl, the heterocycloalkyl, the heteroarylene and the heterocycloalkylene group as defined above, depending on the required valency of the heterocyclic group which will be readily apparent to the skilled person.

As used herein, "halogen" or "halo" represents fluoro, chloro, bromo, or iodo.

Various groups are referred to as being "optionally substituted" in the context of this description. Unless indicated otherwise, these groups may carry one or more than one, such as e.g. one, two, three or four substituents. It will be understood that the maximum number of substituents is limited by the number of attachment sites available on the substituted moiety. Unless defined otherwise in the specific context, these groups carry preferably not more than two substituents and may, in particular, carry only one substituent. Moreover, unless specifically defined otherwise, it is preferred that the optional substituents are absent.

The compounds of formula (I) for use in accordance with the invention have the following structure

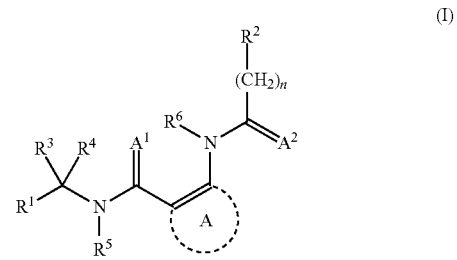

(I)

The variables in formula (I) are defined as follows.

n is selected from 0, 1, 2 or 3, preferably 1 or 2, more preferably 1.

$R^1$ represents a carbocyclic group or heterocyclic group, both of which are optionally substituted by one or more groups independently selected from C1-6 alkyl, C2-6 alkenyl, C2-6 alkynyl, and C1-6 alkoxy. Any of the alkyl, alkenyl, alkynyl or alkoxy substituents is optionally further substituted with 1 to 3 fluoro atoms or with an aryl, heteroaryl, cycloalkyl or heterocycloalkyl group. General preference is given to an optionally substituted carbocyclic group as $R^1$.

The optionally substituted carbocyclic group for $R^1$ is preferably a monocyclic or fused bicyclic ring, in particular a monocyclic ring having 5 or 6 members or a bicyclic ring having 8 to 10 members, among which the monocyclic ring is more preferred. Generally, it is an aryl or cycloalkyl, in particular aryl. Particularly preferred as $R^1$ is an optionally substituted phenyl.

The optionally substituted heterocyclic group for $R^1$ is preferably a monocyclic or fused bicyclic ring, in particular a monocyclic ring having 5 or 6 members or a bicyclic ring having 8 to 10 members, among which the monocyclic ring is more preferred. Preferred as mono- or bicyclic heterocyclic moieties are those containing 1, 2 or 3 heteroatoms independently selected from N, S and O, preferably N. Furthermore, it is preferred that not more than two heteroatoms are present in ring positions adjacent to each other in such a heterocyclic moiety. Generally, the optionally substituted heterocyclic group is a heteroaryl or heterocycloalkyl, in particular heteroaryl such as pyridyl.

The carbocyclic group or heterocyclic group and its preferred embodiments for $R^1$ are optionally substituted by one or more, preferably 1 to 3, and in particular 1, group(s) independently selected from C1-6 alkyl, C2-6 alkenyl, C2-6 alkynyl and C1-6 alkoxy, which alkyl, alkenyl, alkynyl or alkoxy are optionally further substituted with 1 to 3 fluoro atoms or with an aryl, heteroaryl, cycloalkyl or heterocycloalkyl group. The optional substituents are preferably selected from C1-6 alkyl, C2-6 alkenyl, C2-6 alkynyl and C1-6 alkoxy, which alkyl, alkenyl, alkynyl or alkoxy are optionally further substituted with 1 to 3 fluoro atoms, and further preferred as the optional substituent is C1-6 alkyl, optionally further substituted with 1 to 3 fluoro atoms, and particularly preferred is methyl as the optional substituent.

$R^2$ represents a carbocyclic group or heterocyclic group, both of which are optionally substituted, or a group -$Q^1$-$L^1$-$Q^2$, wherein $Q^1$ is a carbocyclic group or a heterocyclic group, both of which are optionally substituted, $L^1$ is absent or represents a linking group of the formula —$(CR^9R^{10})_p$—, wherein p is selected from 1, 2, 3 or 4, $R^9$ and $R^{10}$, independently for each occurrence, are selected from H and C1-6 alkyl, and wherein one or more of the $CR^9R^{10}$ moieties may be replaced by one or more groups selected from —NH—, —N(CH$_3$)—, —O—, —S—, —C(O)—O—, —O—C(O)—, —C(O)—NH—, —NH—C(O)—, or —C(O)—; and $Q^2$ is a carbocyclic group or a heterocyclic group, both of which are optionally substituted;

wherein each optionally substituted carbocyclic group and heterocyclic group may carry 1 to 3 substituents independently selected from C1-6 alkyl, C1-6 alkenyl. C1-6 alkynyl, oxo (=O), halogen, —CF$_3$, —CN, —NO$_2$, —NR$^{11}$R$^{12}$, —CONR$^{11}$R$^{12}$, —COR$^{11}$, —OR$^{11}$, —SR$^{11}$, —SOR$^{11}$, —SO$_2$R$^{11}$,
—SO$_2$NR$^{11}$R$^{12}$, —NR$^{11}$COR$^{12}$, —NR$^{11}$SO$_2$R$^{12}$, —OCOR$^{11}$, —COOR$^{11}$, and —SO$_3$H$_2$;

and wherein each $R^{11}$ and each $R^{12}$ is independently selected from hydrogen or C1-6 alkyl.

If $R^2$ represents an optionally substituted carbocyclic group or an optionally substituted heterocyclic group, it is preferred that the group is a monocyclic or fused bicyclic ring, in particular a monocyclic ring having 5 or 6 members or a bicyclic ring having 8 to 10 members, more preferably a monocyclic ring having 5 or 6 members. Generally, it is selected from aryl, cycloalkyl, heteroaryl or heterocycloalkyl. Examples of particularly preferred groups are phenyl, or a heterocyclic ring having 5 or 6 members and 1 or 2 nitrogen atoms as the heteroatoms, such as pyridinyl or piperazinyl, in particular phenyl.

Preferred substituents for the group $R^2$ representing an optionally substituted carbocyclic group or an optionally substituted heterocyclic group are selected from C1-6 alkyl, in particular methyl, halogen, in particular —F, and —NR$^{11}$COR$^{12}$.

If $R^2$ represents a group -Q-L$^1$-Q$^2$, it is preferred that $Q^1$ is a monocyclic or fused bicyclic ring, in particular a monocyclic ring having 5 or 6 members or a bicyclic ring having 8 to 10 members, more preferably a monocyclic ring having 5 or 6 members. Generally, it is selected from arylene, cycloalkylene, heteroarylene or heterocycloalkylene. Examples of particularly preferred groups are phenylene, piperazindiyl, imidazolidinyl.

Preferred substituents for the optionally substituted group $Q^1$ are selected from C1-6 alkyl, in particular methyl, oxo, and halogen, in particular —F.

Within the definition of $L^1$, p is preferably 1 or 2, $R^9$ and $R^{10}$ are preferably independently selected from hydrogen and methyl, and are in particular hydrogen. It is further preferred that none or one group $CR^9R^{10}$ is replaced by the groups listed above, in particular by —NH—, —N(CH$_3$)—, —C(O)—O—, —O—C(O)—, —C(O)—NH—, or —NH—C(O)—. Examples of particularly preferred groups $L^1$ are a methylene and an ethylene group.

$Q^2$ is preferably a monocyclic or fused bicyclic ring, in particular a monocyclic ring having 3 to 6 members or a bicyclic ring having 8 to 10 members, more preferably a monocyclic ring having 3, 5 or 6 members. Generally, it is selected from aryl, cycloalkyl, heteroaryl or heterocycloalkyl. Examples of particularly preferred groups are phenyl and thiophene.

Preferred substituents for the optionally substituted group $Q^1$ are selected from C1-6 alkyl, in particular methyl, and halogen, in particular —F.

$R^3$ and $R^4$ are independently selected from H, C1-6 alkyl, C2-6 alkenyl, C2-6 alkynyl and C1-6 alkoxy, which alkyl, alkenyl, alkynyl or alkoxy are optionally substituted with 1 to 3 fluoro atoms. Preferred are H and C1-6 alkyl, optionally substituted with 1 to 3 fluoro atoms. As a C1-6 alkyl group, methyl is preferred. It is generally preferred that at least one of $R^3$ and $R^4$ is H. More preferably, either both $R^3$ and $R^4$ are H, or one of $R^3$ and $R^4$ is H and the other one is methyl.

$R^5$ and $R^6$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms. Preferred are H and C1-6 alkyl, optionally substituted with 1 to 3 fluoro atoms. As a C1-6 alkyl group, methyl is preferred. It is most preferred that both $R^5$ and $R^6$ are H.

Alternatively, one of $R^5$ and $R^6$ is as defined above, and the other one is additionally linked to A to form a heterocyclic group fused with A.

For example, $R^5$ may be additionally linked with A and form a heterocyclic group which includes $R^5$ and the moiety —N—C(A$^1$)- to which $R^5$ is attached and which is fused with the cyclic moiety A. Examples of such a fused ring system formed by $R^5$ and A are isoquinoline, quinazoline, isoindole, pyrido[4,3-d]pyrimidine, [2,7]-naphthyridine, [2,6]-naphthyridine, [1,6]-naphthyridine, pthalazine, pyrido[2,3-d]pyridazin and pyrido[3,4-d]pyridazin, which ring systems carry the group $A^1$ as a substituent.

As another example, $R^6$ may be additionally linked with A and form a heterocyclic group which includes $R^6$ and the N-atom to which $R^6$ is attached and which is fused with the cyclic moiety A. Examples of such a fused ring system formed by $R^6$ and A are quinoline, indole and [1,5]-naphthyridine.

However, it is more preferred that both $R^5$ and $R^6$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms, as defined above.

$A^1$ and $A^2$ are independently selected from O, S, NH and NOH, preferably from O and S. More preferably, both $A^1$ and $A^2$ are O.

The cyclic moiety A indicated by the dashed cycle in formula (I) is a carbocyclic group or a heterocyclic group. However, as indicated in the formula it is a carbocyclic group or a heterocyclic group which contains a double bond. The double bond may be part of an aromatic ring. The carbocyclic group and the heterocyclic group are optionally substituted by one or more groups independently selected from C1-6 alkyl, C2-6 alkenyl, C2-6 alkynyl and C1-6 alkoxy. Any of the alkyl, alkenyl, alkynyl or alkoxy substituents is optionally substituted with 1 to 3 fluoro atoms. General preference is given to an optionally substituted carbocyclic group as A.

Specific examples of the moiety A can be selected from the group consisting of benzene, pyrrole, thiophene, furane, pyridine, imidazole, pyrazole, oxazole, thiazole, 1,2,3-triazole, pyrimidine, pyrazine, 1,2,4-triazine, 1,3,5-triazine, 1,2,4-triazine, naphthalene, quinoline, isoquinoline, indole, thienopyridine, thienopyrimidine, pyrrolopyridine, pyrrolopyrimidine, furopyridine and furopyrimidine.

The optionally substituted carbocyclic group for A is preferably a monocyclic ring having 5 or 6 members or a fused bicyclic ring having 8 to 10 members, in particular a monocyclic ring having 5 or 6 members. Moreover, arylenes are generally preferred as A. Particularly preferred as A is an optionally substituted phenyl.

The optionally substituted heterocyclic group for A is preferably a monocyclic or fused bicyclic ring, in particular a monocyclic ring having 5 or 6 members or a bicyclic ring having 8 to 10 members. Preferred as mono- or bicyclic heterocyclic moieties are those containing 1, 2 or 3 heteroatoms independently selected from N, S and O, preferably N. Furthermore, it is preferred that not more than two heteroatoms are present in ring positions adjacent to each other in such a heterocyclic moiety. Generally, the optionally substituted heterocyclic group for A is a heteroaryl such as pyridyl, quinolinyl or isoquinolinyl.

The carbocyclic group or heterocyclic group and its preferred embodiments for A are optionally substituted by one or more, preferably 1 to 3, and in particular 1, group(s) independently selected from C1-6 alkyl, C2-6 alkenyl, C2-6 alkynyl and C1-6 alkoxy, which alkyl, alkenyl, alkynyl or alkoxy are optionally substituted with 1 to 3 fluoro atoms each. The optional substitutents are preferably selected from C1-6 alkyl, optionally substituted with 1 to 3 fluoro atoms, and particularly preferred is methyl as a substituent. However, general preference is given to the absence of a substituent on A.

For example, the compounds of formula (I) may be those of formula (Ia) or (Ib) below:

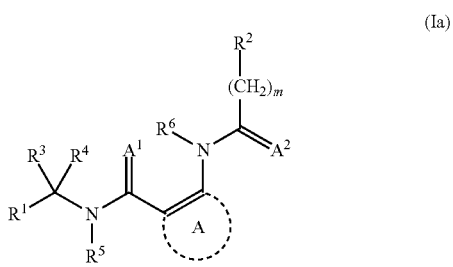

(Ia)

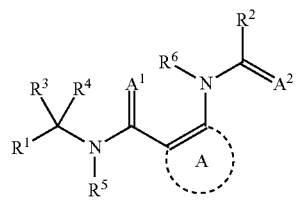

(Ib)

In these formulae, $R^1$, $R^2$, $R^3$, $R^4$, $R^5$, $R^6$, $A^1$, $A^2$, and A are defined as for formula (I), including the preferred definitions given for these variables. In formula (a), m is 1 or 2.

Generally preferred embodiments of the compounds of formula (I) are illustrated in formula (II) below.

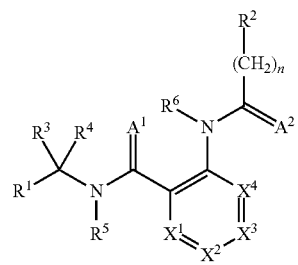

(II)

In this formula, n, $R^1$, $R^2$, $R^3$, $R^4$, $R^5$, $R^6$, $A^1$ and $A^2$ are defined as for formula (I), including the preferred definitions given for these variables.

$X^1$ is selected from N and $CR^a$, $X^2$ is selected from N and $CR^b$, $X^3$ is selected from N and $CR^c$, and $X^4$ is selected from N and $CR^d$, with the proviso that at most 3 of $X^1$, $X^2$, $X^3$ and $X^4$ are N. Preferably, at most 2 and in particular 0 or 1 of $X^1$, $X^2$, $X^3$ and $X^4$ are N. It is most preferred that none of $X^1$, $X^2$, $X^3$ and $X^4$ are N. $R^a$, $R^b$, $R^c$ and $R^d$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms. Preferably $R^a$, $R^b$, $R^c$ and $R^d$ are independently selected from H and C1-6 alkyl, optionally substituted with 1 to 3 fluoro atoms. As alkyl group, methyl is preferred. More preferably, $R^a$, $R^b$, $R^c$ and $R^d$ are all H, or one of $R^a$, $R^b$, $R^c$ and $R^d$ is C1-6 alkyl, in particular methyl, and the other ones are H.

For example, the compounds of formula (II) may be those of formula (IIa) or (IIb) below:

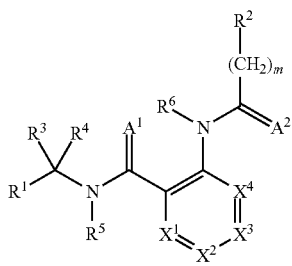

(IIa)

-continued

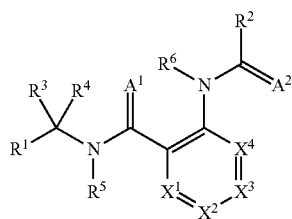
(IIb)

In these formulae, $R^1$, $R^2$, $R^3$, $R^4$, $R^5$, $R^6$, $A^1$, $A^2$, $X^1$, $X^2$, $X^3$ and $X^4$ are defined as for formula (II), including the preferred definitions given for these variables. In formula (IIa), m is 1 or 2.

Further, more preferred embodiments of the compounds of formula (I) are illustrated in formula (III) below.

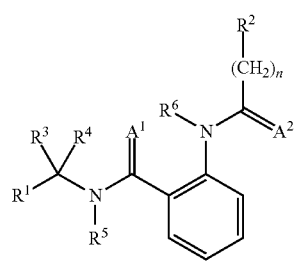
(III)

In this formula, n, $R^1$, $R^2$, $R^3$, $R^4$, $R^5$, $R^6$, $A^1$ and $A^2$ are defined as for formula (I), including the preferred definitions given for these variables.

For example, the compounds of formula (III) may be those of formula (IIIa) or (IIIb) below:

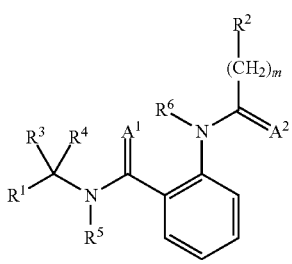
(IIIa)

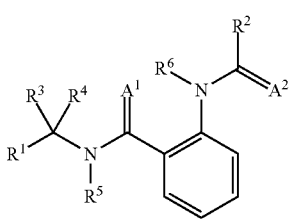
(IIIb)

In these formulae, $R^1$, $R^2$, $R^3$, $R^4$, $R^5$, $R^6$, $A^1$ and $A^2$ are defined as for formula (III), including the preferred definitions given for these variables. In formula (IIIa), m is 1 or 2.

Yet further preferred embodiments of the compounds of formula (I) are illustrated in formula (IV) below.

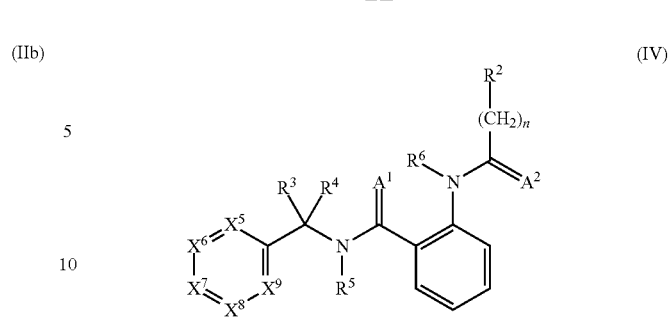
(IV)

In this formula, n, $R^2$, $R^3$, $R^4$, $R^5$, $R^6$, $A^1$ and $A^2$ are defined as for formula (I), including the preferred definitions given for these variables.

$X^5$ is selected from N and $CR^e$, $X^6$ is selected from N and $CR^f$, $X^7$ is selected from N and $CR^g$, $X^8$ is selected from N and $CR^h$, and $X^9$ is selected from N and $CR^i$ with the proviso that at most 3 of $X^5$, $X^6$, $X^7$, $X^8$ and $X^9$ are N. Preferably, at most 2 and in particular 0 or 1 of $X^5$, $X^6$, $X^7$, $X^8$ and $X^9$ are N. $R^e$, $R^f$, $R^g$, $R^h$ and $R^i$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms. Preferably, $R^e$, $R^f$, $R^g$, $R^h$ and $R^i$ are independently selected from H and C1-6 alkyl, optionally substituted with 1 to 3 fluoro atoms. As alkyl group, methyl is preferred. It is particularly preferred that either all of $R^e$, $R^f$, $R^g$, $R^h$ and $R^i$ are H, or that one of them, e.g. $R^g$, is methyl, and the others are H.

For example, the compounds of formula (IV) may be those of formula (IVa) or (IVb) below:

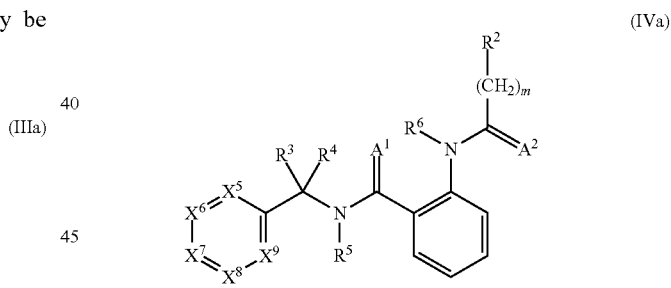
(IVa)

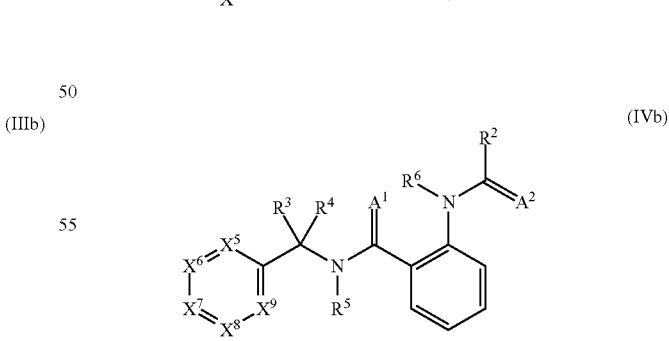
(IVb)

In these formulae, $R^2$, $R^3$, $R^4$, $R^5$, $R^6$, $A^1$, $A^2$, $X^5$, $X^6$, $X^7$, $X^8$ and $X^9$ are defined as for formula (IV), including the preferred definitions given for these variables. In formula (IVa), m is 1 or 2.

Particularly preferred embodiments of the compounds of formula (I) are illustrated in formula (V) below.

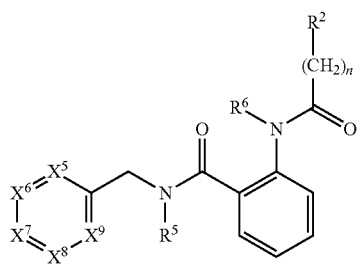

(V)

In this formula, n, $R^2$, $R^5$ and $R^6$ are defined as for formula (I), including the preferred definitions given for these variables.

$X^5$ is selected from N and $CR^e$, $X^6$ is selected from N and $CR^f$, $X^7$ is selected from N and $CR^g$, $X^8$ is selected from N and $CR^h$, and $X^9$ is selected from N and $CR^i$ with the proviso that at most 3 of $X^5$, $X^6$, $X^7$, $X^8$ and $X^9$ are N. Preferably, at most 2 and in particular 0 or 1 of $X^5$, $X^6$, $X^7$, $X^8$ and $X^9$ are N. Most preferred is the case where none of $X^5$, $X^6$, $X^7$, $X^8$ and $X^9$ is N. $R^e$, $R^f$, $R^g$, $R^h$ and $R^i$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms. Preferably, $R^e$, $R^f$, $R^g$, $R^h$ and $R^i$ are independently selected from H and C1-6 alkyl, optionally substituted with 1 to 3 fluoro atoms. As alkyl group, methyl is preferred. It is particularly preferred that either all of $R^e$, $R^f$, $R^g$, $R^h$ and $R^i$ are H, or that one of them, e.g. $R^g$, is methyl, and the others are H.

For example, the compounds of formula (V) may be those of formula (Va) or (Vb) below:

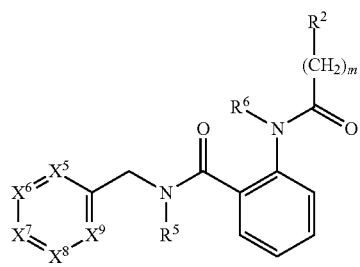

(Va)

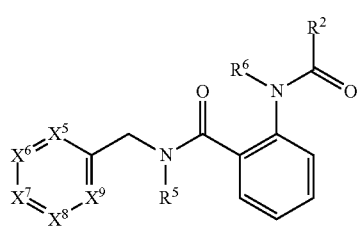

(Vb)

In these formulae (Va), $R^2$, $R^5$, $R^6$, $X^5$, $X^6$, $X^7$, $X^8$ and $X^9$ are defined as for formula (V), including the preferred definitions given for these variables. In formula (Va), m is 1 or 2.

In accordance with an even further preferred embodiment, $X^5$ and $X^9$ in the above formulae (V), (Va) and (Vb) are both CH, $X^6$ is selected from N and $CR^f$, $X^7$ is selected from N and $CR^g$, and $X^8$ is selected from N and $CR^h$, with the proviso that at most 1 of $X^6$, $X^7$ and $X^8$ is N. More preferred is the case where none of $X^6$, $X^7$ and $X^8$ is N. $R^f$, $R^g$ and $R^h$ are independently selected from H and methyl optionally substituted with 1 to 3 fluoro atoms.

Specific preferred compounds of formula (I) in the context of the invention are those illustrated in the following:

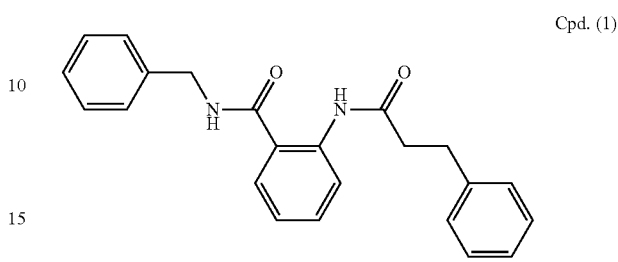

Cpd. (1)

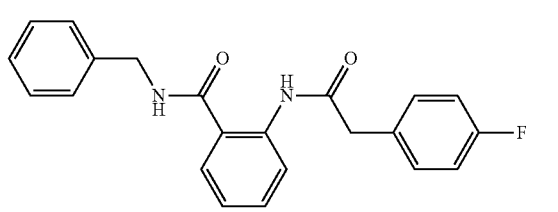

Cpd. (2)

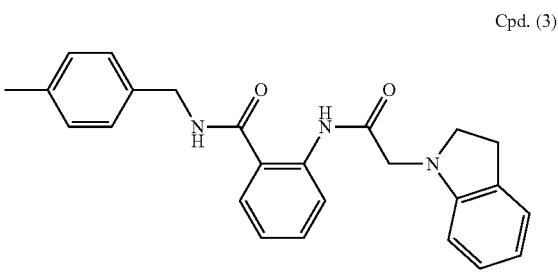

Cpd. (3)

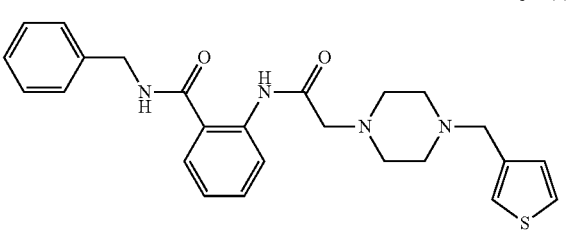

Cpd. (4)

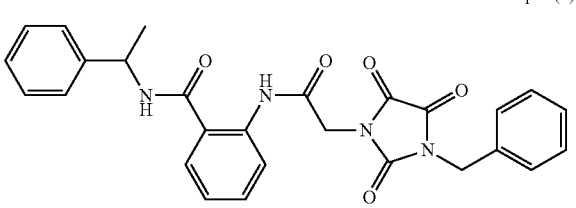

Cpd. (5)

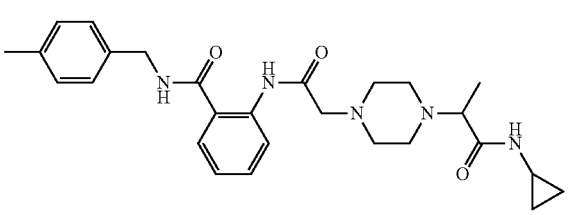

Cpd. (6)

-continued
Cpd. (7)
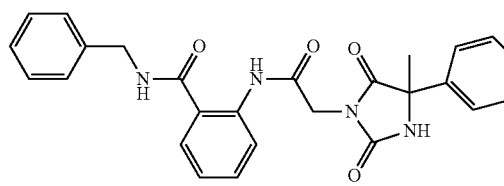
Cpd. (8)
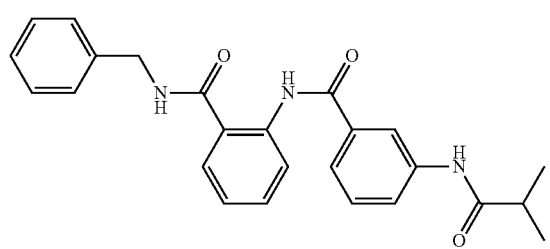
Cpd. (9)
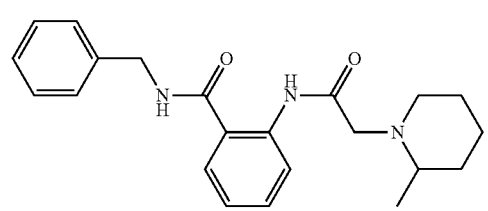
Cpd. (10)
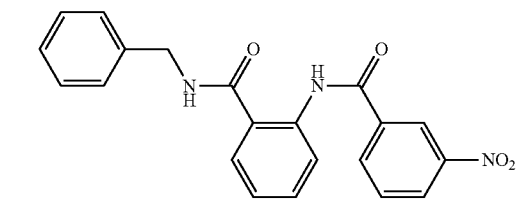
Cpd. (11)
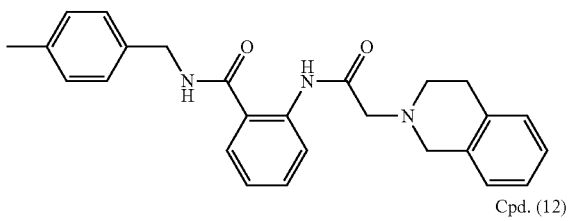
Cpd. (12)
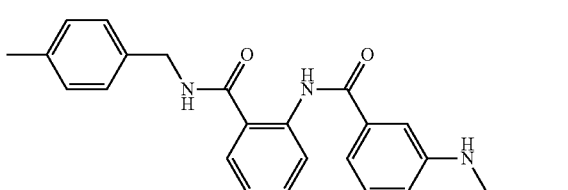
Cpd. (13)
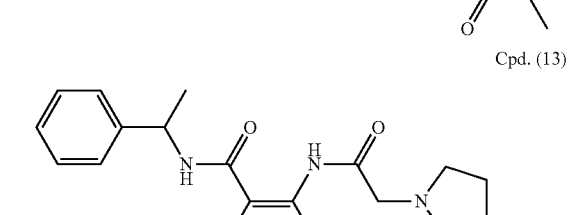
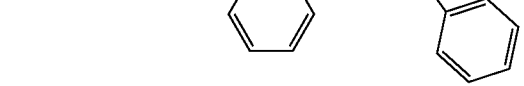
-continued
Cpd. (14)
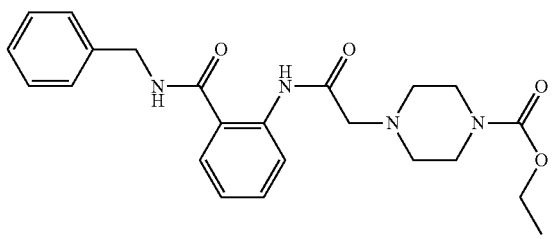
Cpd. (15)
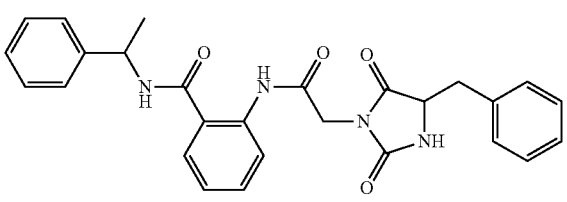
Cpd. (16)
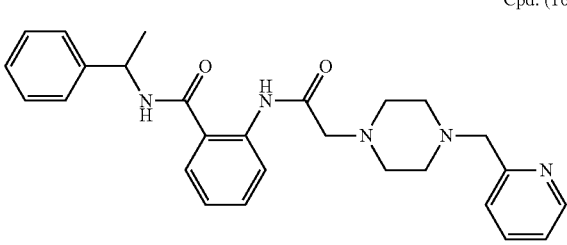
Cpd. (17)
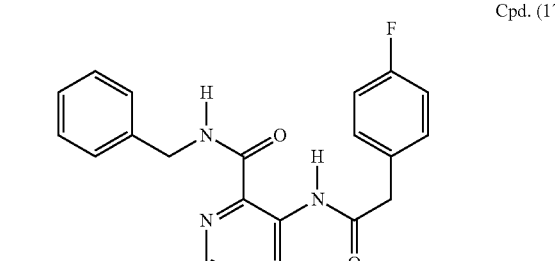
Cpd. (18)
Cpd. (19)
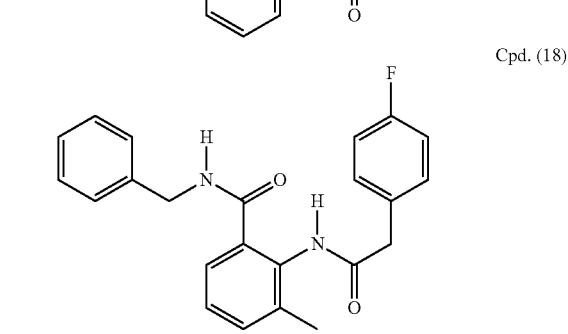
The compounds in accordance with the invention are either commercially available (e.g. from Alinda Chemical, Ltd., (Moscow, Russia; www.alinda.ru) or Enamine Ltd.

(Kiev, Ukraine; www.enamine.net)), or can be prepared using readily available reactants by standard chemical reactions.

Compounds of general formula (I) (including the preferred formulae (I Ia, Ib, II, IIa, IIb, III, IIIa, IIIb, IV, IVa, IVb, V, Va, Vb and the specific exemplary compounds) may exist in the form of different isomers, in particular stereoisomers (including geometric isomers (or cis-trans isomers), enantiomers and diastereomers) or tautomers. All such isomers of the compounds according to the invention are contemplated as being part of the present invention, either in admixture or in pure or substantially pure form. As for stereoisomers, the invention embraces mixtures (such as racemic forms) and the isolated optical isomers of the compounds according to the invention. The racemic forms can be resolved by physical methods, such as, e.g., fractional crystallization, separation or crystallization of diastereomeric derivatives or separation by chiral column chromatography.

The scope of the invention also embraces compounds of the general formula (I) (including the preferred formulae Ia, Ib, II, IIa, IIb, III, IIIa, IIIb, IV, IVa, IVb, V, Va, Vb and the specific exemplary compounds) for the described use, in which one or more atoms are replaced by a specific isotope of the corresponding atom. For example, the invention encompasses compounds of formula (I), in which one or more hydrogen atoms (e.g., all hydrogen atoms) are replaced by deuterium atoms (i.e., $^2$H; also referred to as "D"), although the presence of naturally occurring hydrogen atoms or $^1$H hydrogen atoms in the compounds of formula (I) is preferred. In general, it is preferred that none of the atoms in the compounds of formula (I) is replaced by a specific isotope.

As noted above, salts of the compounds of formula (I) (including the preferred formulae Ia, Ib, II, IIa, IIb, III, IIIa, IIIb, IV, IVa, IVb, V, Va, Vb and the specific exemplary compounds) are also suitable for use in the context of the invention. It will be understood that these salts are generally pharmaceutically acceptable salt forms of these compounds which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the compounds of formula (I) (including the preferred formulae (Ia, Ib, II, IIa, IIb, III, IIIa, IIIb, IV, IVa, IVb, V, Va, Vb and the specific exemplary compounds) are also suitable for use in the context of the invention as solids in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Prodrugs of compounds of formula (I) (including the preferred formulae Ia, Ib, II, IIa, IIb, III, IIIa, IIIb, IV, IVa, IVb, V, Va, Vb and the specific exemplary compounds) that can be used in the present invention are generally pharmaceutically acceptable derivatives which have chemically or metabolically cleavable groups and become, by solvolysis or under physiological conditions, the compounds used in the present invention which are pharmaceutically active in vivo. Prodrugs of compounds that can be used in the present invention may be formed in a conventional manner with a functional group of the compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). Prodrugs include acid derivatives well known to the person skilled in the art, such as, for example, esters prepared by reaction of the parent acidic compound with a suitable alcohol, or amides prepared by reaction of the parent acid compound with a suitable amine. When a compound employed in the present invention, in particular a compound of the general formula (I), has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholinoethylester or N,N-diethylglycolamido-ester. When a compound employed in the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)—C$_3$H$_7$, —OC(=O)-(tert-butyl), —OC(=O)—C$_{15}$H$_{31}$, —OC(=O)—CH$_2$CH$_2$COONa, —O(C=O)—CH(NH$_2$)CH$_3$ or —OC(=O)—CH$_2$—N(CH$_3$)$_2$. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

As noted above, one main aspect of the present invention concerns the compounds of formula (I) (including the preferred formulae Ia, Ib, II, IIa, IIb, III, IIIa, IIIb, IV, IVa, IVb, V, Va, Vb and the specific exemplary compounds) or salts or solvates thereof for use in preventing or treating a retroviral infection and/or a disease associated with a retroviral infection. Preferably, the disease associated with said retroviral infection is causally related to said infection, so that therapeutically addressing the viral infection will also ameliorate said disease associated with the retroviral infection. Retroviral infections are well known in the art and are caused by retroviruses which are RNA viruses that amplify their genomes within the host cell by using the enzyme reverse transcriptase to produce DNA from its RNA genome. The retroviruses are grouped into the genera Alpharetrovirus, Betaretrovirus, Gammaretrovirus, Deltaretrovirus, Epsilonretrovirus, Lentivirus and Spumavirus. Preferably, the retroviral infection is caused by a lentivirus.

Thus, in a preferred embodiment, the retroviral infection is a lentiviral infection such as, e.g., a bovine lentiviral infection, an equine lentiviral infection, a feline lentiviral infection, an ovine/caprine lentiviral infection or a primate lentiviral infection, such as, e.g. a human immunodeficiency virus (HIV) infection. In other terms, and in a more preferred embodiment, the invention also relates to the compounds of formula (I) or salts or solvates thereof for use in preventing or treating a HIV-infection and/or a disease associated with a HIV-infection.

As used herein, the term "HIV-infection" generally encompasses infection of a host, particularly a human host, by the human immunodeficiency virus (HIV) family of retroviruses including, but not limited to, HIV-1, HIV-2 (previously also known as HTLV-III/LAV/ARV, LAV-1, LAV-2). Preferably, the HIV-infection is a HIV-1 and/or HIV-2 infection and more preferred a HIV-1 infection "HIV" can be used herein to refer to any strains, forms, subtypes, classes and variations in the HIV family. Thus, "treatment" of a HIV-infection and/or a disease associated with a HIV-infection will encompass the treatment of a person who is a carrier of any of the HIV family of retroviruses or a person who is diagnosed of active AIDS, as well as the treatment or prophylaxis of AIDS-related conditions in such persons. AIDS is also an example of a disease associated with an HIV-infection. The skilled person is well-aware of the pathology of AIDS including initiation, progression and clinical outcomes. A carrier of HIV may be identified by any method known in the art. For example, a person can be identified as an HIV carrier on the basis that the person is anti-HIV antibody positive, or is HIV-positive, or has symptoms of AIDS. That is, "treating HIV-infection" should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4 positive T cells), and AIDS (which is defined by more serious AIDS-defining illnesses and/or a decline in the circulating CD4 cell count to below a level that is compatible with effective immune function). In addition, "preventing or treating of a disease associated with an HIV-infection" will also encompass treating suspected infection by HIV after suspected past exposure to HIV by e.g., contact with HIV-contaminated blood, as a result of blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "preventing" also encompasses treating a person who has not been diagnosed as having a HIV infection but is believed to be at risk of infection by HIV. Diseases associated with an HIV-infection can generally be treated by eradicating the primary cause thereof, optionally in conjunction with medicaments known in the art that are registered for the treatment of such secondary causes.

The skilled person is well-aware of the pathology of a HIV-infection and diseases associated with a HIV-infection and hence is in the position to devise a therapy according to general principles known in the art and described, for example, elsewhere herein.

It will be understood by the skilled reader that the compounds identified herein, including salts, solvates and prodrugs thereof can be administered singly or in combinations of two or more of them. In addition, while the compounds identified herein are sufficient for preventing or treating a retroviral infection and/or a disease associated with a retroviral infection, it is also envisaged that they can be combined with further active agents. Preferably, said further active agents are also used for the treatment of retroviral infections. For example, and in the case of a HIV-infection, the compounds of the invention can be combined with known anti-HIV agents and/or therapies as described herein above (combination therapy HAART, NARTIs or NRTIs, NNRTIs, and/or protease inhibitors), but may also be combined with anti-HIV agents and/or therapies not yet approved for therapeutic use, such as e.g., anti-HIV vaccines. The compounds of the invention can either be administered before, simultaneously with or after a known anti-HIV therapy. In case the compounds of the invention and the known anti-HIV active agents are used simultaneously, their administration may be performed at the same time, e.g. administering an admixture of both active agents, before or after administration of one of the compounds.

In a further embodiment, the invention also relates to a method of preventing or treating a retroviral infection and/or a disease associated with a retroviral infection comprising the administration of the compounds of formula (I) (including the preferred formulae (Ia, Ib, II, IIa, IIb, III, IIIa, IIIb, IV, IVa, IVb, V, Va, Vb and the specific exemplary compounds) or salts or solvates thereof to a subject in need thereof, thereby preventing or treating said retroviral infection and/or said disease associated with a retroviral infection. The definitions and combinations of technical features described for the above embodiment relating to the use of the compounds of formula (I) or salts or solvates thereof in the treatment of a retroviral infection and/or a disease associated with a retroviral infection apply mutatis mutandis also to this embodiment.

A compound of formula (I) (including the preferred formulae (Ia, Ib, II, IIa, IIb, III, IIIa, IIIb, IV, IVa, IVb, V, Va, Vb and the specific exemplary compounds) or a salt or solvate thereof can be administered as such, but is typically administered in the form of a pharmaceutical composition comprising a compound of formula (I) (including the preferred formulae (Ia, Ib, II, IIa, IIb, III, IIIa, IIIb, IV, IVa, IVb, V, Va, Vb and the specific exemplary compounds) or a salt or solvate thereof. Such a pharmaceutical composition may further comprise pharmaceutically acceptable excipients. Pharmaceutically acceptable excipients that may be used in the formulation of the pharmaceutical compositions may comprise carriers, vehicles, diluents, solvents such as monohydric alcohols such as ethanol, isopropanol and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintegrants, glidants, lubricating agents, buffering agents, emulsifiers, wetting agents, suspending agents, sweetening agents, colourants, flavours, coating agents, preservatives, antioxidants, processing agents, drug delivery modifiers and enhancers such as calcium phosphate, magnesium state, talc, monosaccharides, disaccharides, starch, gelatine, cellulose, methylcellulose, sodium carboxymethyl cellulose, dextrose, hydroxypropyl-β-cyclodextrin, polyvinylpyrrolidone, low melting waxes, ion exchange resins. Other suitable pharmaceutically acceptable excipients are described in Remington's Pharmaceutical Sciences, 15th Ed., Mack Publishing Co., New Jersey (1991). Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal, oral or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, individual response of the patient to be treated, severity of the disease to be treated, the activity and bioavailability of the particular compound applied and other drugs being administered concurrently. Pharmaceutically active matter may be present in amounts between 1 ng and 10 mg/kg body weight per dose; however, doses below or above this exemplary range are envisioned, especially considering the aforementioned factors. If the regimen is a continuous infusion, it is preferably in the range of 1 μg to 10 mg units per kilogram of body weight per minute.

The pharmaceutical compositions of the invention can be produced in a manner known per se to the skilled person or as described, for example, in Remington's Pharmaceutical Sciences, 15th Ed., Mack Publishing Co., New Jersey (1991).

Various preferred embodiments of the invention as described above shall be summarized in the following items:

1. A compound of the following formula (I), or a salt, solvate or prodrug thereof,

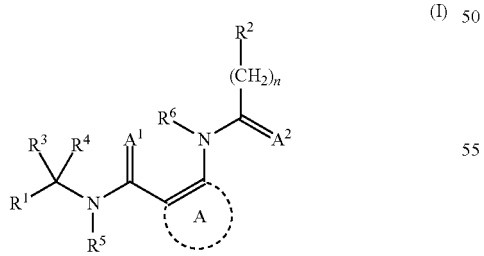

for use in preventing or treating a retroviral infection, wherein:
n is selected from 0, 1, 2 or 3;
$R^1$ represents a carbocyclic group or heterocyclic group, both of which are optionally substituted by one or more groups independently selected from C1-6 alkyl, C2-6 alkenyl, C2-6 alkynyl and C1-6 alkoxy, with any of the alkyl, alkenyl, alkynyl or alkoxy substituents being optionally further substituted with 1 to 3 fluoro atoms or with an aryl, heteroaryl, cycloalkyl or heterocycloalkyl group;
$R^2$ represents a carbocyclic group or heterocyclic group, both of which are optionally substituted, or a group $-Q^1-L^1-Q^2$, wherein $Q^1$ is a carbocyclic group or a heterocyclic group, both of which are optionally substituted, $L^1$ is absent or represents a linking group of the formula $-(CR^9R^{10})_p-$, wherein p is selected from 1, 2, 3 or 4, $R^9$ and $R^{10}$, independently for each occurrence, are selected from H and C1-6 alkyl, and wherein one or more of the $CR^9R^{10}$ moieties may be replaced by one or more groups selected from $-NH-$, $-N(CH_3)-$, $-O-$, $-S-$, $-C(O)-O-$, $-O-C(O)-$, $-C(O)-NH-$, $-NH-C(O)-$, or $-C(O)-$; and $Q^2$ is a carbocyclic group or a heterocyclic group, both of which are optionally substituted:
wherein each optionally substituted carbocyclic group and heterocyclic group may carry 1 to 3 substituents independently selected from C1-6 alkyl, C2-6 alkenyl, C2-6 alkynyl, oxo (=O), halogen, $-CF_3$, $-CN$, $-NO_2$, $-NR^{11}R^{12}$, $-CONR^{11}R^{12}$, $-COR^{11}$, $-OR^{11}$, $-SR^1$, $-SOR^{11}$, $-SO_2R^{11}$, $-SO_2NR^{11}R^{12}$, $-NR^{11}COR^{12}$, $-NRSO_2R^{12}$, $-OCOR^{11}$, $-COOR^{11}$, and $-SOH_2$;
and wherein each $R^{11}$ and each $R^{12}$ is independently selected from hydrogen or C1-6 alkyl;
$R^3$ and $R^4$ are independently selected from H, C1-6 alkyl, C2-6 alkenyl, C2-6 alkynyl and C1-6 alkoxy, which alkyl, alkenyl, alkynyl or alkoxy are optionally substituted with 1 to 3 fluoro atoms;
$R^5$ and $R^6$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms, or one of $R^5$ and $R^6$ is as defined above, and the other one is additionally linked to A to form a heterocyclic group fused with A;
$A^1$ and $A^2$ are independently selected from O, S, NH and NOH; and
the cyclic moiety A indicated by the dashed cycle in formula (I) is a carbocyclic group containing the double bond indicated in the formula which double bond may be part of an aromatic system or a heterocyclic group containing the double bond indicated in the formula which double bond may be part of an aromatic system, both of which are optionally substituted by one or more groups independently selected from C1-6 alkyl, C2-6 alkenyl, C2-6 alkynyl and C1-6 alkoxy.

2. The compound of item 1, wherein $A^1$ and $A^2$ are O.
3. The compound of item 1 or 2, wherein either both $R^3$ and $R^4$ are H, or one of $R^3$ and $R^4$ is H and the other one is methyl.
4. The compound of any of items 1 to 3, wherein $R^5$ is H.
5. The compound of any of items 1 to 4 wherein $R^5$ is H.
6. The compound of any of items 1 to 5, wherein $R^1$ is an optionally substituted monocyclic carbocyclic group having 5 or 6 ring members or an optionally substituted monocyclic heterocyclic group having 5 or 6 ring members.
7. The compound of any of items 1 to 6, wherein A is a monocyclic ring having 5 or 6 ring members.
8. The compound of any of items 1 to 7, wherein the compound of formula (I) is a compound of formula (Ia):

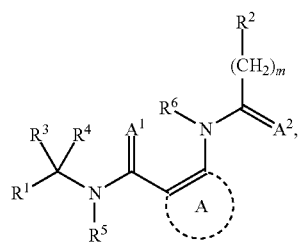

(Ia)

wherein $R^1$, $R^2$, $R^3$, $R^4$, $R^5$, $R^6$, $A^1$, $A^2$, and A are defined as for formula (I), and m is 1 or 2.

9. The compound of any of items 1 to 7, wherein the compound of formula (I) is a compound of formula (Ib):

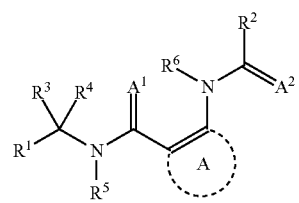

(Ib)

wherein $R^1$, $R^2$, $R^3$, $R^4$, $R^5$, $R^6$, $A^1$, $A^2$, and A are defined as for formula (I).

10. The compound of any of items 1 to 6, wherein the compound of formula (I) is a compound of formula (IV):

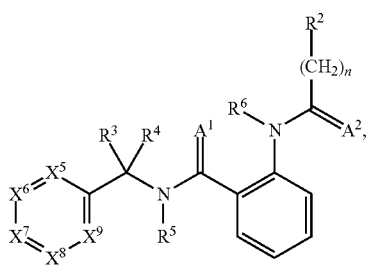

(IV)

wherein n, $R^2$, $R^3$, $R^4$, $R^5$, $R^6$, $A^1$ and $A^2$ are defined as for formula (I), $X^5$ is selected from N and $CR^e$, $X^6$ is selected from N and $CR^f$, $X^7$ is selected from N and $CR^g$, $X^8$ is selected from N and $CR^h$, and $X^g$ is selected from N and $CR^i$, with the proviso that at most 3 of X, $X^6$, $X^7$, $X^8$ and $X^9$ are N;

$R^e$, $R^f$, $R^g$, $R^h$ and $R^i$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms.

11. The compound of item 10, wherein $X^5$ and $X^9$ are both CH, $X^6$ is selected from N and $CR^f$, $X^7$ is selected from N and $CR^g$ and $X^6$ is selected from N and $CR^h$, with the proviso that at most 1 of $X^6$, $X^7$ and $X^8$ is N, and $R^f$, $R^g$ and $R^h$ are independently selected from H and methyl optionally substituted with 1 to 3 fluoro atoms.

12. The compound of item 1, which is selected from one of the following compounds:

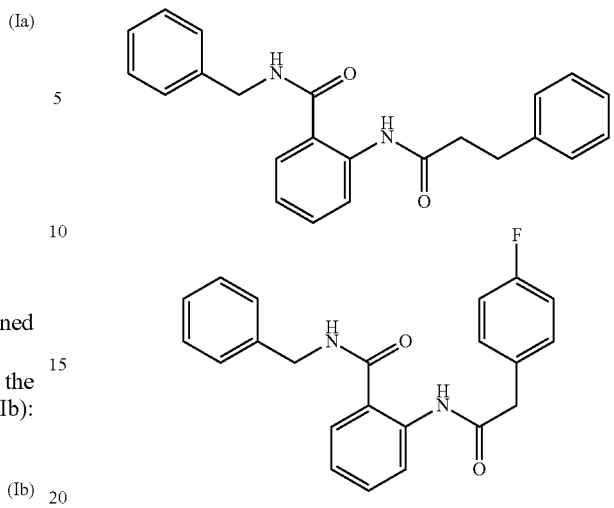

13. The compound of any of items 1 to 12 or a salt, solvate or prodrug thereof, wherein the retroviral infection to be prevented or treated is a lentiviral infection.

14. The compound of any of items 1 to 12 or a salt, solvate or prodrug thereof, wherein the retroviral infection to be prevented or treated is a HIV infection.

In this specification, a number of documents including manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples, which are merely illustrative and are not to be construed as a limitation of the scope of the present invention.

THE FIGURES SHOW

FIG. 1: ELISA assay

A sandwich assay was developed to screen for compounds that inhibit the binding of a4b7 to gp120. Without inhibitors, gp120 and a4b7 bind and this complex can be identified by addition of a mouse anti-gp120 mAb (step 3). This a4b7*gp120anti-gp120 mAb complex is then sequestered on the bottom surface of a 96 welled-plate coated with an anti-mouse secondary mAb (step 4). The complex is then detected by addition of a biotinylated primary mAb against a4b7 (step 5) and detected using an HRP-avidin (step 6). A positive binding event is identified by the presence of HPR activity within each well. The addition of an inhibitor (step 2) blocks the binding between gp120 and a4b7 leading to a lack or reduction of HRP activity as shown in steps 2-5 at the bottom of the figure.

Figure 2:
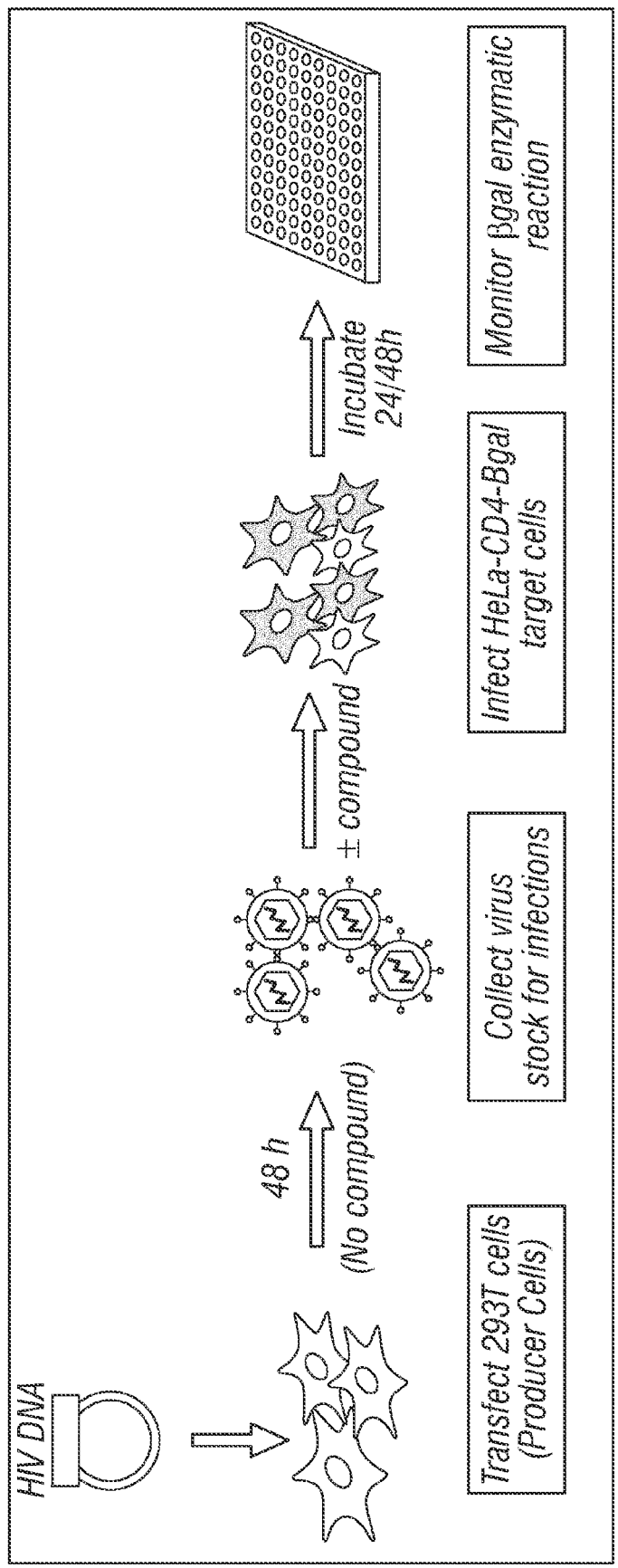

FIG. 2: Experimental outline to evaluate HIV infectivity in a HeLa reporter cell line HIV-1 particles are produced in 293T cells transfected with R9 HIV DNA in the absence of test compounds. Particles are collected, titrated by measuring the amount of p24 antigen and frozen until their use. In the infectivity assay HeLa-CD4-Bgal cells are preincubated for 20 min in the absence or presence of test compounds, and the viral particles are added. Infectivity is monitored with a beta-galactosidase enzymatic reaction 36 hours after infection. Test compounds and virus are left with the cells throughout the entire infection period.

EXAMPLES

Example 1 gp120 Binding to a4b7

Studies were conducted to study the binding of gp120 to the integrin α4β7 (or a4b7; alpha4 beta7 as used herein above) and to develop a high-throughput assay to screen for compounds that interfere with the binding of HIV associated glycoprotein gp120 and the integrin α4β7.

A. Materials.

General methods were used to obtain the necessary cells, proteins, antibodies and reagents.

Antibodies.

A goat HIV1 anti-gp120 polyclonal antibody (ab21179) was obtained from Abcam. Mouse anti-gp120 monoclonal antibodies (mAbs) were obtained from Abcam [HIV1 gp120](ab13411) and Prospec [HIV-1 gp120](ANT-151). Mouse mAbs were used in the ELISA assay and the goat polyclonal antibody was used for protein production. A rat mAb against integrin α4β7 [DATK32](ab25329) was obtained from Abcam Inc. In addition, mouse antibodies against the human integrin α4 [44H6](ab220) and human integrin β7 [8G2](mca5238Z) were obtained from Abcam Inc. and AbD Serotec Inc., respectively, and used for protein purification. The integrin α4β7 mAb was also labeled with biotin using EZ-Link Sulfo-NHS biotinylation kit (21425) from ThermoScientific using the procedures described in the manufacturers protocol.

Gp120 Protein.

HIV-1 gp120 plasmid was also obtained containing the gp120 gene from an M cell-tropic HIV-1 ADA strain. The recombinant envelope gp120 glycoprotein was also previously produced in the Baculovirus Expression System (Invitrogen) on a hollow-fiber filter cell device (Filter Cell Systems Inc) in Sf9 cells (Orbigen Inc.). Crude recombinant envelope gp120 glycoprotein was purified by prep-fast protein liquid chromatography (FPLC). This method was used to prepare the gp120 protein for prior studies. Reapplication of the method delivered 4.2 mg of gp120 protein with a purity of over 95% purity by SDS PAGE analysis using a SilverQuest kit (Invitrogen) for detection.

Alpha4 Beta7 (α4β7) or LPAM-1 Protein.

Recombinant human α4β7 integrin was purchased from R&D Systems (Catalog Number: 5397-A3). Larger quantities of the α4β7 integrin were by in house. Recombinant expression of both subunits α4 and β7 was accomplished by preparation plasmids containing the α4 (protein accession #P13612) and β7 (protein accession #P26010) both containing a C-terminal 6×His tag. Both proteins were expressed in CHO cells using conventional methods and were purified to ≥98% purity (SDS PAGE analysis) by sequential His-tag purification on NTA-agarose followed by repetitive size exclusion purification using a Sephadex G-200 column. The 6×His tags were removed prior to size exclusion purification. The purity of each subunit was evaluated by SDS-PAGE analysis and both subunits were purified to over 98% purity using a SilverQuest kit (Invitrogen) for detection. The α4β7 integrin was reconstituted was prepared by incubation of a 1:1 mixture of the α4 and β7 subunits followed by size exclusion purification by three passes on a Sephadex G-200 column. An anti-α4β7 mAb was used to identify the fractions containing the α4β7 integrin. This method was used to provide 12.5 mg of the α4β7 integrin with greater than 96% purity. The activity of the α4β7 integrin was determined by using the methods established by R&D Systems Inc., as given by measuring the ability of the immobilized α4β7 integrin to support the adhesion of VCAM-1 transfected Chinese hamster ovary (CHO) cells. When $5 \times 10^4$ cells per well are added to rhIntegrin α4β7 coated plates (10 μg/mL, 100 μL/well), between 60-80% will adhered in 1 h at 37° C. This procedure is described in the product catalog for the α4β7 integrin (R&D Systems Inc.). All assays were conducted with protein produced in our laboratories and was checked once in triplicate against the commercial protein.

Reagents.

HRP-NeutrAvidin (21124) from ThermoScientific and QuantaBlu Fluorogenic Peroxidase Substrate (15169) from ThermoScientific were used to develop the ELISA assays. All compounds were provided and stocked at 10 mg/mL in DMSO and stored at −80° C. until used. Buffers were all prepared as sterile media and were stored for less than 24 h. All other reagents, plates, or devices are noted as used.

C. ELISA Analysis.

It was previously demonstrated that co-immunoprecipitation analyses as analyzed via western blots were a viable means to evaluate the binding of gp120 to α4β7 in human cell lysates. This method was advanced into an ELISA format and applied to screen the number of compounds provided within the research period.

It was determined that the direction of the assay was not critical and antibodies can be used against both gp120 and the α4β7 integrins in any order. Based on these studies, an optimized ELISA assay as outlined in FIG. 1, below, was designed.

C.1. Assay Development.

The studies began by screening for the optimal protein concentrations for the method. The studies were conducted in goat anti-mouse IgG coated black React-Bind 96 welled-plates (R&D Biosystems), referred to herein as the anti-mouse IgG plate. Twelve stock solutions were prepared containing a 1:1 stoichiometric mixture of gp120 and α4β7 integrin in PBS at pH 7.2 as given by 0 μM or control, 0.001 μM, 0.01 μM, 0.01 μM, 0.05 μM, 0.1 μM, 0.5 μM. 1 μM, 2.5 μM, 5 μM, 10 μM and 25 μM in protein (step 1, FIG. 1). A 200 μL aliquot of each stock solutions was then loaded across a 96 welled plate and treated either with 20 μL of PBS pH 7.2 (control) or 20 μL of a 100 μM stock solution of repandusinic acid (RA: compound whose anti-HIV activity is to be tested) in PBS pH 7.2 containing 1% DMSO. Three repetitions were run for both the control and positive or repandusinic acid treated experiments. The final concentration of repandusinic acid in each positive well was 10 μM. The plate was incubated for 4 h at 4° C. on a plate mixer at a speed that created a vortex in each well.

During this time, repandusinic binds to blocks the formation of the α4β7.gp120 complex (step 2, FIG. 1). This process provided a plate containing the antigens, or so called antigen plate.

In parallel, the anti-mouse IgG plate was washed 3 times with 200 μL of wash buffer (PBS pH 7.2, containing 0.05% Tween 20) and treated with 100 μL of a 0.5 μg/mL stock of the mouse anti-gp120 mAb in PBS pH 7.2. Two mAbs were tested (see Materials Section above). Data was reported using a combination from three repetitions from each mAb, affording an average over six experiments, as indicated by step 3 (FIG. 1). This process delivered the binding plate.

After incubating the plate for 1 h at 23° C. on a plate mixer at a speed that created a vortex in each well, each well drained by aspiration and washed three times with 200 μL of wash buffer. The contents of the antigen plate (above) were transferred to the complementary wells on the binding plate. The binding plate was shaken for 1 h at 23° C. on a plate mixer at a speed that created a vortex in each well, as indicated by step 4 (FIG. 1).

Each well of the binding plate was aspirated and rinsed three times with 200 μL of wash buffer. The wells were charged with 100 μL of a 0.1 μg/mL of the rat anti α4β7 mAb and the plate was shaken for 1 h at 37° C. (step 5, FIG. 1). This process was then repeated using 100 μL of 0.2 μg/mL solution of the HRP-conjugated strepavidin (step 6, FIG. 1). The HRP activity was developed using QuantaBlu fluorogenic peroxidise substrate (ThermoScientific) and evaluated on a HTS7000 plate reader (Perkin Elmer). Using this method it was determined that the ideal concentration of gp120 and α4β7 was 0.5-1.0 μM.

C.2. Optimization.

Then the assay was exhaustively tested by screening the inhibition of the binding of gp120 and α4β7 by repandusinic acid. Stock solutions of repandusinic acid (10× stock solutions) were prepared at 0 μM or control, 0.01 μM, 0.1 μM, 0.1 μM, 0.5 μM, 1 μM, 5 μM, 10 μM, 25 μM, 50 μM, 100 μM and 250 μM).

Using this gradient, we were able to identify the following optimized protocol.

Step 1: Prepare the antigen plate
a. Prepare a PBS stock solution containing 1 μM gp120 and 1 μM α4β7
b. Add a 200 μL aliquot to each well of the antigen plate.

Step 2: Add the inhibitor.
a. Add 20 μL of a 10× stock of the inhibitor in PBS pH 7.2 containing 1% DMSO
b. Incubate at 4° C. for 6 h with shaking. This delivers the antigen plate.

Step 3: Prepare the binding plate.
a. Aspirate each well of the binding plate
b. Wash three times with 200 μL of wash buffer (PBS pH 7.2, containing 0.05% Tween 20).
c. Add 100 μL of a 0.5 μg/mL stock of the mouse anti-gp120 mAb in PBS pH 7.2
d. Shake for 1 h at 23° C.

Step 4: Sequester the gp120*α4β7 complex.
a. Aspirate each well of the binding plate.
b. Wash three times with 200 μL of wash buffer.
c. Transfer the contents of the antigen plate to the corresponding wells in the binding plate.
d. Shake for 1 h at 23° C.

Step 5: Develop the binding plate.
a. Aspirate each well of the binding plate.
b. Wash three times with 200 μL of wash buffer.
c. Add 100 μL of a 0.1 μg/mL of the rat anti-α4β7 mAb.
d. Shake for 1 h at 37° C.
e. Aspirate each well of the binding plate.
f. Wash three times with 200 μL of wash buffer.
g. Add 100 μL of 0.2 μg/mL solution of the HRP-conjugated strepavidin
h. Shake for 1 h at 37° C.
i. Aspirate each well of the binding plate.
j. Wash three times with 200 μL of wash buffer.
k. Develop using QuantaBlu fluorogenic peroxidase substrate (ThermoScientific)
l. Evaluate the fluorescence output on a HTS7000 plate reader (Perkin Elmer).

The inhibition of the binding of gp120 and α4β7 can be serialized and conducted in a 96 welled plate format.

Application of the Gp120 and Integrin α4β7 Association Assay

The ELISA assay was applied to screen the compounds in the table, below, to further characterize their activity against the binding of HIV associated glycoprotein gp120 and the integrin α4β7.

D. Implementation.

The five-step assay developed was applied to screen the compounds in the table below. These materials were stored at −80° C. over the research period and were shown to be stable and retain purity by LC/MS analysis prior to use. The experiments were run in triplicate using two antibodies against gp120.

Results:

| Compound No. | IC50 a4b7 (nM) |
|---|---|
| 1 | 0.33 |
| 2 | 0.89 |
| 3 | 19.20 |
| 4 | 0.27 |
| 5 | 0.64 |
| 6 | 0.61 |
| 7 | 0.46 |
| 8 | 0.98 |
| 9 | 1.23 |
| 10 | 1.53 |
| 11 | 1.64 |
| 12 | 2.19 |
| 13 | 2.45 |
| 14 | 2.64 |
| 15 | 2.80 |
| 16 | 4.67 |

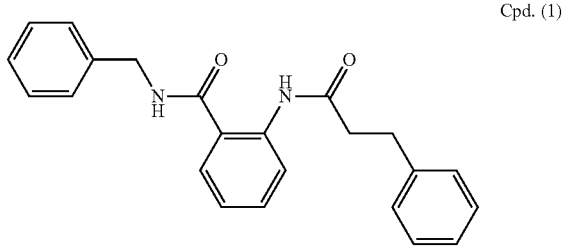

Cpd. (1)

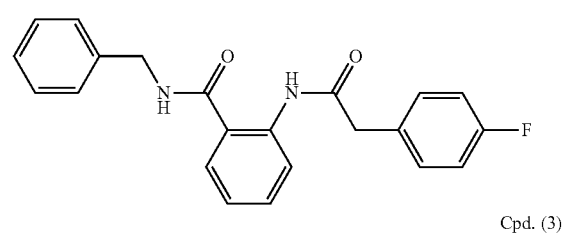

Cpd. (2)

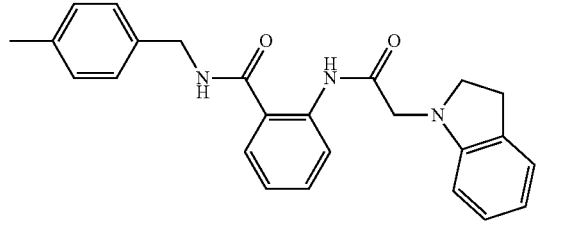

Cpd. (3)

-continued
Cpd. (4)
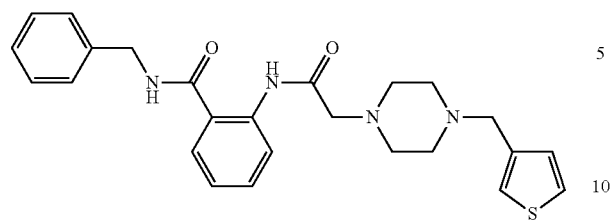
Cpd. (5)
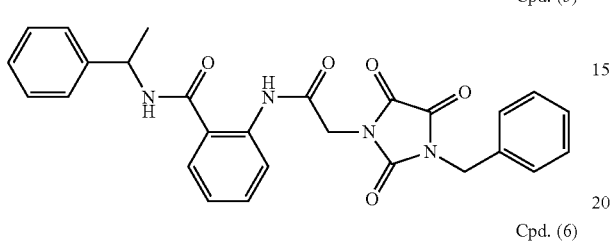
Cpd. (6)
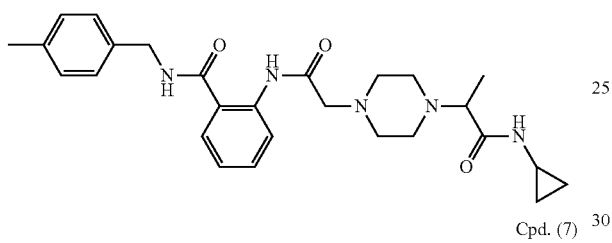
Cpd. (7)
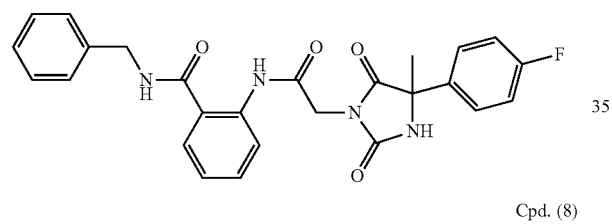
Cpd. (8)
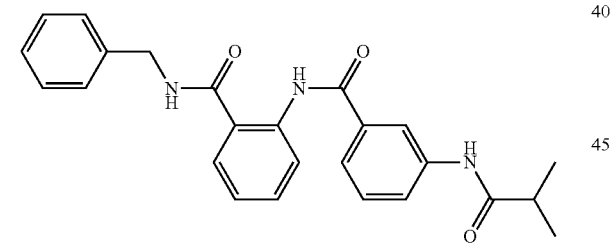
Cpd. (9)
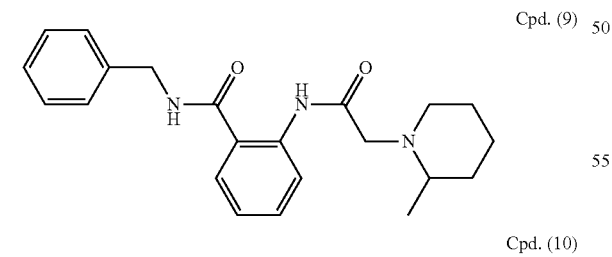
Cpd. (10)
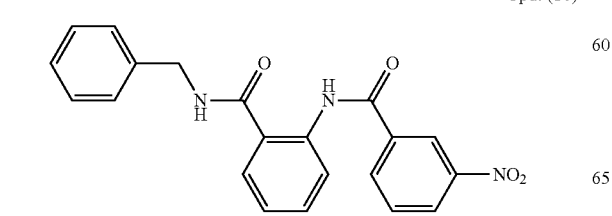
-continued
Cpd. (11)
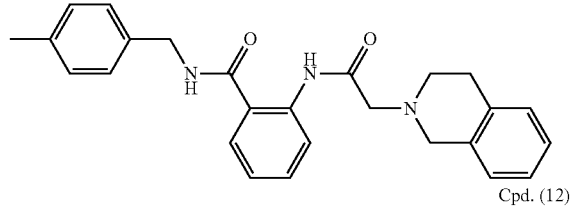
Cpd. (12)
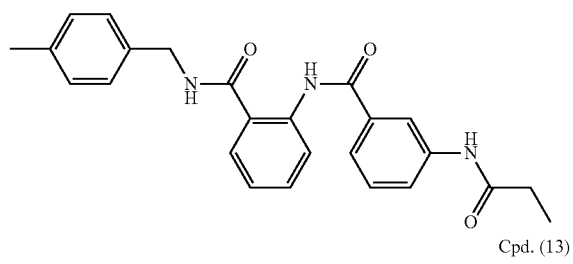
Cpd. (13)
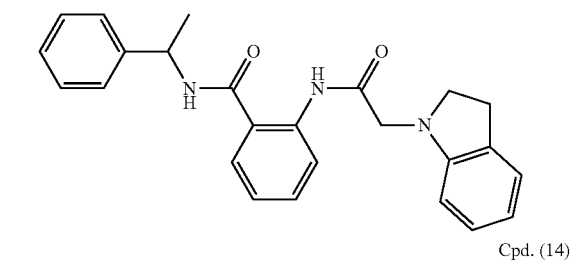
Cpd. (14)
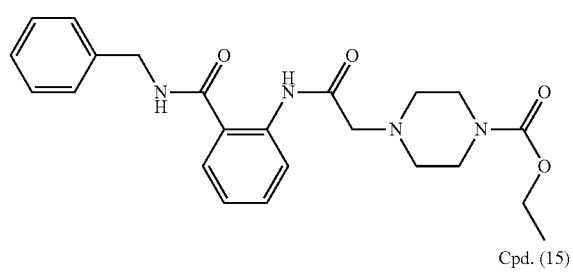
Cpd. (15)
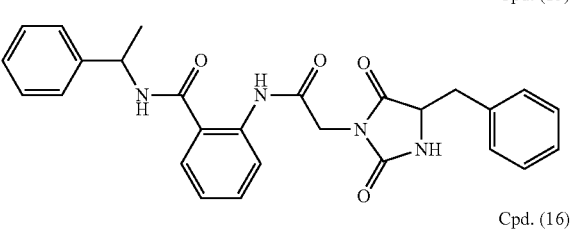
Cpd. (16)
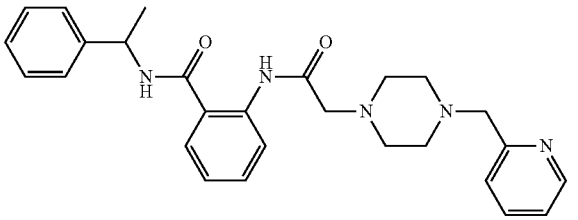
Example 2
Antiviral Assay
Phytohemagglutinin (PHA)-P-activated PBMC were infected with the reference lymphotropic HIV-1-LAI strain (Wain-Hobson et al., Science, vol. 252, no. 5008, pp. 961-

965 (1991)). This virus was amplified in vitro with PHA-P-activated blood mononuclear cells. Viral stocks were titrated using PHA-P-activated PBMC, and 50% tissue culture infectious doses (TCID50) was calculated using Karber's formula. PBMC were pretreated for 30 min by two concentrations of each molecule and infected with 125 TCID50 of this HIV-1 strain. AZT and T20 were used as reference anti-HIV molecule. Molecules were maintained throughout the culture, and cell supernatants were collected at day 7 post-infection and stored at −20° C. Viral replication was measured by quantifying reverse transcriptase (RT) activity in these cell culture supernatants using the Lenti RT activity kit (Cavidi). In parallel, cytotoxicity was evaluated on day 7 in uninfected PHA-P-activated PBMC using the colorimetric methyl-tetrazolium salt assay (MTS/PMS; Promega). Experiments were performed in triplicate and the inhibition of viral replication of the compounds was calculated using SoftMaxPro software (Molecular Devices Inc. CA, USA).

Results

| Virus: | HIV-1-LAI |
|---|---|
| Reference mol. 1 | AZT (Zidovudine) |
| Reference mol. 2 | T20 (Enfuvirtide) |

Dilutions in Cell Culture Medium Containing 0.1% DMSO (Final Concentration)

| Conc. (nM) | AZT | T20 | Conc. (nM) | Cpd. 2 |
|---|---|---|---|---|
| 1000 | 100% ± 0 | 100% ± 0 | 10000 | 87% ± 9 |
| 200 | 100% ± 0 | 100% ± 0 | 2000 | 22% ± 3 |
| 40 | 100% ± 1 | 100% ± 0 | 400 | 6% ± 16 |
| 8 | 95% ± 7 | −13% ± 4 | 80 | 4% ± 8 |
| 1.6 | 59% ± 11 | 5% ± 15 | 16 | −6% ± 22 |
| 0.32 | 16% ± 7 | −9% ± 3 | 3.2 | 16% ± 4 |
| ED50 (nM) | 1.3 | 28.9 | ED50 (nM) | 5590 ± 441 |
| ED70 (nM) | 2.5 | 30 | ED70 (nM) | 8021 ± 710 |
| ED90 (nM) | 6.6 | 31.7 | ED90 (nM) | 9826 ± 246 |

Example 3

Infectivity Assays

Compounds were evaluated with a HeLa reporter cell line containing the bacterial b-galactosidase gene inserted in the cell chromosome under control of the viral LTR. Upon infection with HIV, these cells express the bacterial enzyme, whose activity is revealed in the form of luminescence. These assays reveal blocks in the virus life cycle that result in lower production of the Tat-induced b-galactosidase gene in reporter cells, but do not detect the effect of maturation and late-stage inhibitors such as proteinase inhibitors (PIs). HIV-1 R9 (CXCR4-tropic strain) was used in these experiments to challenge cells. Viruses were first produced by transfection of 293T cells with a plasmid DNA expressing HIV-1. Viral particles were harvested and frozen until use. Infectivity assays were performed incubating cells in the absence or presence of compounds for 20 min before addition of virus. Upon infection, virus and compounds were left with the cells for the entire period of infection (36 h). At that time the extent of infection was evaluated using a luminescent substrate of Bgal. FIG. 2 depicts the experimental outline used to evaluate the anti-HIV activity of lead compounds. Controls with known ARVs include AZT, a reverse-transcriptase inhibitor (RTI), and the HIV integrase inhibitor raltegravir. Controls with vehicle alone are also included Results:

| | Inhibition of HIV infectivity in % | | | | | | |
|---|---|---|---|---|---|---|---|
| Compound | Concentration µM: 0.008 | 0.04 | 0.2 | 1 | 5 | 25 | 125 |
| Cpd. 2 | 69.28 | 51.94 | 62.3 | 60.66 | 13.81 | 2.76 | 4.1 |
| Cpd. 3 | 67.64 | 58.63 | 61.6 | 42.22 | 12.81 | 2.39 | 0.19 |

| Compound | EC50, µM | EC90, µM |
|---|---|---|
| Cpd. 2 | 3.4 | 30.6 |
| Cpd. 3 | 1.69 | 15.2 |

The invention claimed is:

1. A method of treating a retroviral infection, wherein the retroviral infection is a human immunodeficiency virus (HIV) infection, the method comprising administering a pharmaceutically effective amount of a compound of the following formula (IV), or a salt, or solvate thereof, to a patient in need thereof;

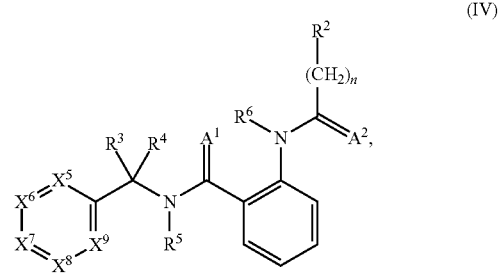

(IV)

wherein:
n is selected from 0, 1, 2 or 3;
$R^2$ represents a carbocyclic group or heterocyclic group, both of which are optionally substituted, or
a group -$Q^1$-$L^1$-$Q^2$, wherein $Q^1$ is a carbocyclic group or a heterocyclic group, both of which are optionally substituted, $L^1$ is absent or represents a linking group of the formula —$(CR^9R^{10})_p$—, wherein p is selected from 1, 2, 3 or 4, $R^9$ and $R^{10}$, independently for each occurrence, are selected from H and C1-6 alkyl, and wherein one or more of the $CR^9R^{10}$ moieties may be replaced by one or more groups selected from —NH—, —N(CH$_3$)—, —O—, —S—, —C(O)—O—, —O—C(O)—, —C(O)—NH—, —NH—C(O)—, or —C(O)—; and $Q^2$ is a carbocyclic group or a heterocyclic group, both of which are optionally substituted;

wherein each optionally substituted carbocyclic group and heterocyclic group may carry 1 to 3 substituents independently selected from C1-6 alkyl, C2-6 alkenyl, C2-6 alkynyl, oxo (=O), halogen, —CF$_3$, —CN, —NO$_2$, —NR$^{11}$R$^{12}$, —CONR$^{11}$R$^{12}$, —COR$^{11}$, —OR$^{11}$, —SR$^{11}$, —SOR$^{11}$, —SO$_2$R$^{11}$, —SO$_2$NR$^{11}$R$^{12}$, —NR$^{11}$COR$^{12}$, —NR$^{11}$SO$_2$R$^{12}$, —OCOR$^{11}$, —COOR$^{11}$, and —SO$_3$H$_2$;

and wherein each R$^{11}$ and each R$^{12}$ is independently selected from hydrogen or C1-6 alkyl;

R$^3$ and R$^4$ are independently selected from H, C1-6 alkyl, C2-6 alkenyl, C2-6 alkynyl and C1-6 alkoxy, which alkyl, alkenyl, alkynyl or alkoxy are optionally substituted with 1 to 3 fluoro atoms;

R$^5$ and R$^6$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms, or one of R$^5$ and R$^6$ is as defined above, and the other one is additionally linked to A to form a heterocyclic group fused with A;

A$^1$ and A$^2$ are O; and

X$^5$ is CR$^e$, X$^6$ is CR$^f$, X$^7$ is CR$^g$, X$^8$ is CR$^h$, and X$^9$ is CR$^i$;

R$^f$, R$^g$, R$^h$ and R$^i$ are independently selected from H, C1-6 alkyl, C2-6 alkenyl, C2-6 alkynyl and C1-6 alkoxy, which alkyl, alkenyl, alkynyl or alkoxy may be optionally substituted with 1 to 3 fluoro atoms.

2. The method of claim 1, wherein A$^1$ and A$^2$ are O.

3. The method of claim 1, wherein either both R$^3$ and R$^4$ are H, or one of R$^3$ and R$^4$ is H and the other one is methyl.

4. The method of claim 1, wherein R$^5$ is H.

5. The method of claim 1, wherein R$^6$ is H.

6. The method of claim 1, wherein the compound is selected from the group consisting of:

Cpd. (1)

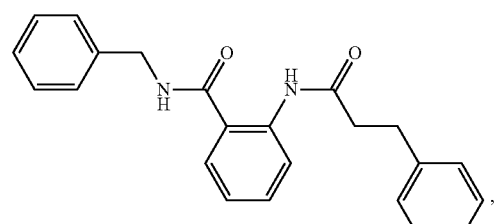

Cpd. (2)

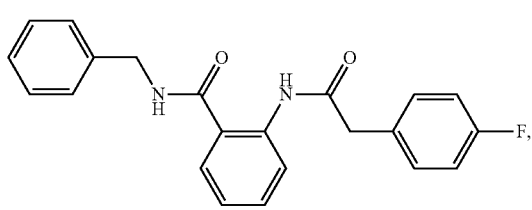

Cpd. (3)

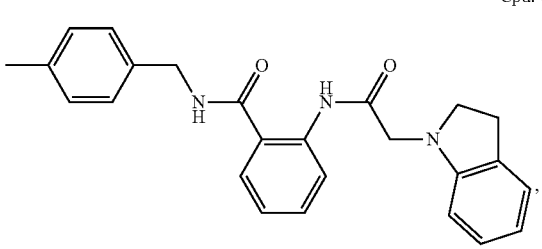

Cpd. (4)

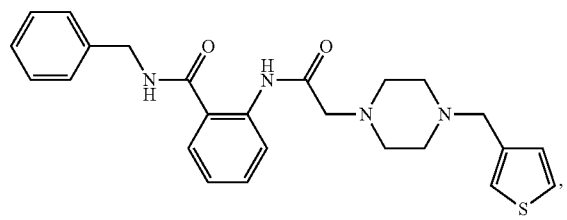

Cpd. (5)

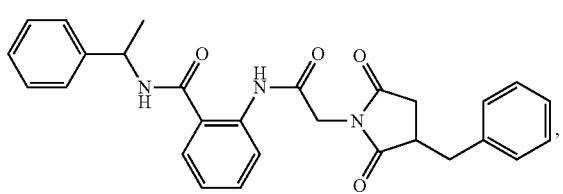

Cpd. (6)

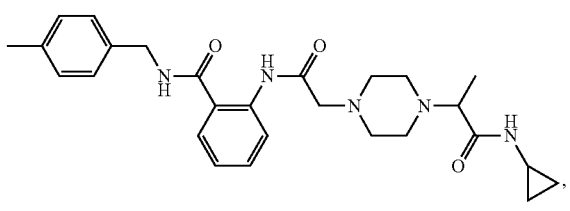

Cpd. (7)

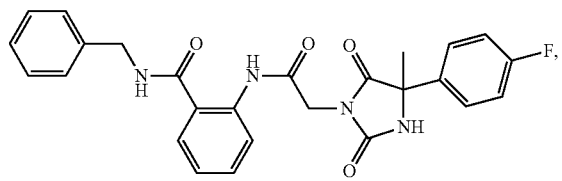

Cpd. (8)

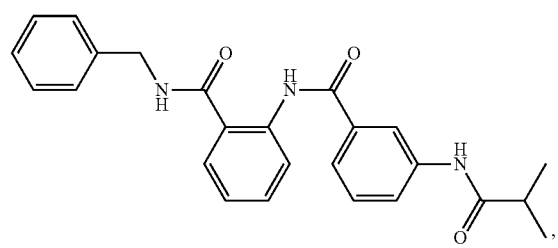

Cpd. (9)

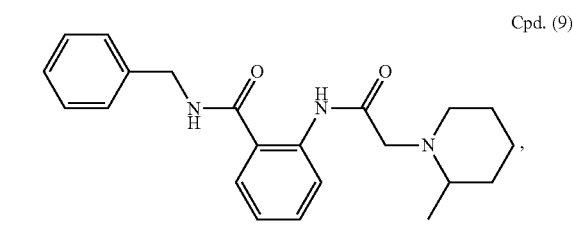

-continued
Cpd. (10)
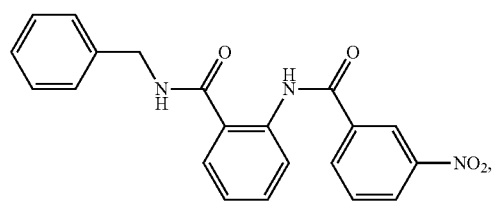
Cpd. (11)
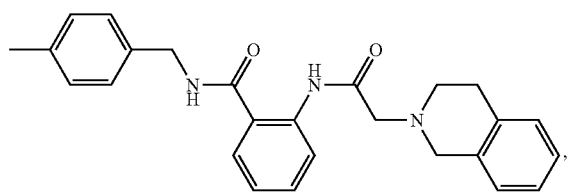
Cpd. (12)
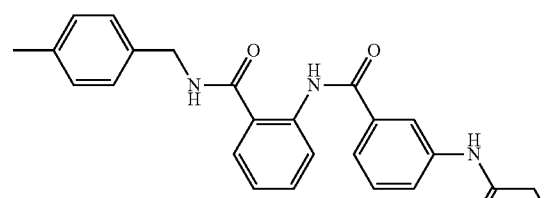
Cpd. (13)
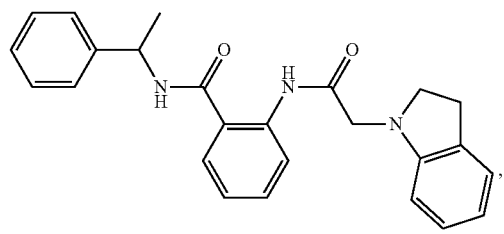
-continued
Cpd. (14)
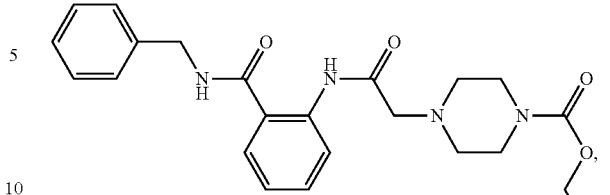
Cpd. (15)
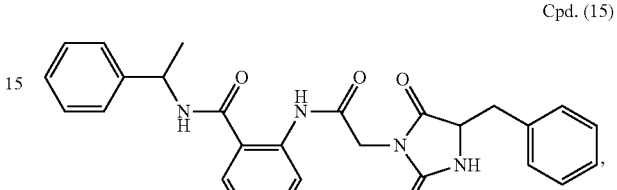
and
Cpd. (16)
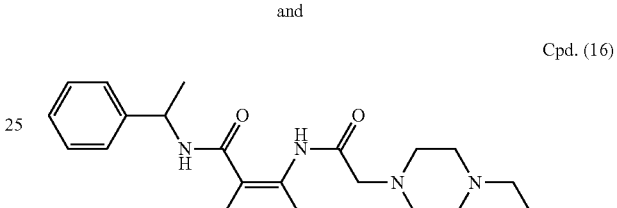
7. The method of claim 1, wherein the binding of HIV associated glycoprotein gp120 and integrin alpha4 beta7 (α4β7) is inhibited.
8. The method of claim 1, wherein the HIV viral replication is inhibited.
9. The method of claim 1, wherein the HIV infectivity is inhibited.
* * * * *